(12) United States Patent
Kikuchi

(10) Patent No.: US 11,045,079 B2
(45) Date of Patent: Jun. 29, 2021

(54) ENDOSCOPE DEVICE, IMAGE PROCESSING APPARATUS, IMAGE PROCESSING METHOD, AND PROGRAM

(71) Applicant: OLYMPUS CORPORATION, Hachioji (JP)

(72) Inventor: Sunao Kikuchi, Akiruno (JP)

(73) Assignee: OLYMPUS CORPORATION, Tokyo (JP)

(*) Notice: Subject to any disclaimer, the term of this patent is extended or adjusted under 35 U.S.C. 154(b) by 396 days.

(21) Appl. No.: 16/039,802

(22) Filed: Jul. 19, 2018

(65) Prior Publication Data

US 2018/0344136 A1 Dec. 6, 2018

Related U.S. Application Data

(63) Continuation of application No. PCT/JP2017/005175, filed on Feb. 13, 2017.

(30) Foreign Application Priority Data

Mar. 14, 2016 (WO) .................. PCT/JP2016/058002

(51) Int. Cl.
*A61B 1/04* (2006.01)
*A61B 1/07* (2006.01)
(Continued)

(52) U.S. Cl.
CPC .............. *A61B 1/04* (2013.01); *A61B 1/0005* (2013.01); *A61B 1/00009* (2013.01);
(Continued)

(58) Field of Classification Search
CPC ....... A61B 1/0163; A61B 1/0172; A61B 1/06; A61B 1/0638; A61B 1/0676; A61B 1/07; A61B 1/0653
See application file for complete search history.

(56) References Cited

U.S. PATENT DOCUMENTS

2005/0228231 A1* 10/2005 MacKinnon ....... G02B 23/2461
600/180
2006/0232668 A1 10/2006 Horn et al.
(Continued)

FOREIGN PATENT DOCUMENTS

JP 2003010114 A 1/2003
JP 2006297093 A 11/2006
(Continued)

OTHER PUBLICATIONS

International Search Report (ISR) dated Apr. 25, 2017 issued in International Application No. PCT/JP2017/005175.
(Continued)

*Primary Examiner* — Matthew J Kasztejna
(74) *Attorney, Agent, or Firm* — Holtz, Holtz & Volek PC

(57) ABSTRACT

An endoscope device is disclosed which includes an image processing unit that generates a first image corresponding to light in a green wavelength band on the basis of an imaging signal generated by an imaging device when a light source unit emits first illumination light or second illumination light, and generates a second image corresponding to light in other one of wavelength bands. Resolution of the first image obtained when the light source unit emits the first illumination light is equal to or higher than resolution of the first image obtained when the light source unit emits the second illumination light, and resolution of the second image obtained when the light source unit emits the second illumination light is higher than resolution of the second image obtained when the light source unit emits the first illumination light.

17 Claims, 30 Drawing Sheets

(51) Int. Cl.
*A61B 1/06* (2006.01)
*A61B 1/045* (2006.01)
*G02B 23/24* (2006.01)
*A61B 1/00* (2006.01)

(52) U.S. Cl.
CPC ...... *A61B 1/00096* (2013.01); *A61B 1/00163* (2013.01); *A61B 1/043* (2013.01); *A61B 1/045* (2013.01); *A61B 1/0638* (2013.01); *A61B 1/0646* (2013.01); *A61B 1/0676* (2013.01); *A61B 1/07* (2013.01); *G02B 23/24* (2013.01); *G02B 23/2461* (2013.01)

(56) References Cited

U.S. PATENT DOCUMENTS

| | | |
|---|---|---|
| 2008/0239070 A1 | 10/2008 | Westwick et al. |
| 2011/0273548 A1* | 11/2011 | Uchiyama ......... A61B 1/00009 348/68 |
| 2012/0215066 A1 | 8/2012 | Akiyama et al. |
| 2013/0286176 A1 | 10/2013 | Westwick et al. |
| 2016/0249019 A1 | 8/2016 | Westwick et al. |
| 2016/0270643 A1 | 9/2016 | Sasaki |
| 2016/0278613 A1 | 9/2016 | Kuriyama |
| 2017/0064257 A1 | 3/2017 | Westwick et al. |
| 2017/0064258 A1 | 3/2017 | Westwick et al. |

FOREIGN PATENT DOCUMENTS

| | | |
|---|---|---|
| JP | 2012081048 A | 4/2012 |
| JP | 2015116328 A | 6/2015 |
| JP | 2015119765 A | 7/2015 |
| WO | 2011162111 A1 | 12/2011 |

OTHER PUBLICATIONS

Written Opinion dated Apr. 25, 2017 issued in International Application No. PCT/JP2017/005175.

\* cited by examiner

FIG.29

| TYPES OF COMPLEMENTARY COLOR PIXELS | COMPLEMENTARY COLOR PIXEL 1 | COMPLEMENTARY COLOR PIXEL 2 | FIRST WAVELENGTH BAND | SECOND WAVELENGTH BAND | EFFECT |
|---|---|---|---|---|---|
| ONE TYPE | CYAN | — | GREEN | BLUE | IMPROVEMENT IN GREEN RESOLUTION IN WHITE LIGHT IMAGING<br>IMPROVEMENT IN BLUE RESOLUTION IN SPECIAL LIGHT IMAGING |
| | YELLOW | — | GREEN | RED | IMPROVEMENT IN GREEN RESOLUTION IN WHITE LIGHT IMAGING<br>IMPROVEMENT IN RED RESOLUTION IN SPECIAL LIGHT IMAGING |
| TWO TYPES | CYAN | MAGENTA | GREEN | BLUE | IMPROVEMENT IN GREEN RESOLUTION IN WHITE LIGHT IMAGING<br>IMPROVEMENT IN BLUE RESOLUTION IN SPECIAL LIGHT IMAGING<br>(MAGENTA PIXEL CAN BE USED AS BLUE PIXEL IN SPECIAL LIGHT IMAGING) |
| | CYAN | YELLOW | GREEN | BLUE | IMPROVEMENT IN GREEN RESOLUTION IN WHITE LIGHT IMAGING<br>IMPROVEMENT IN BLUE RESOLUTION IN SPECIAL LIGHT IMAGING<br>(YELLOW PIXEL CAN BE USED AS GREEN PIXEL IN SPECIAL LIGHT IMAGING) |
| | YELLOW | CYAN | GREEN | RED | IMPROVEMENT IN GREEN RESOLUTION IN WHITE LIGHT IMAGING<br>IMPROVEMENT IN RED RESOLUTION IN SPECIAL LIGHT IMAGING<br>(CYAN PIXEL CAN BE USED AS GREEN PIXEL IN SPECIAL LIGHT IMAGING) |
| | YELLOW | MAGENTA | GREEN | RED | IMPROVEMENT IN GREEN RESOLUTION IN WHITE LIGHT IMAGING<br>IMPROVEMENT IN RED RESOLUTION IN SPECIAL LIGHT IMAGING<br>(MAGENTA PIXEL CAN BE USED AS RED PIXEL IN SPECIAL LIGHT IMAGING) |

FIG.30

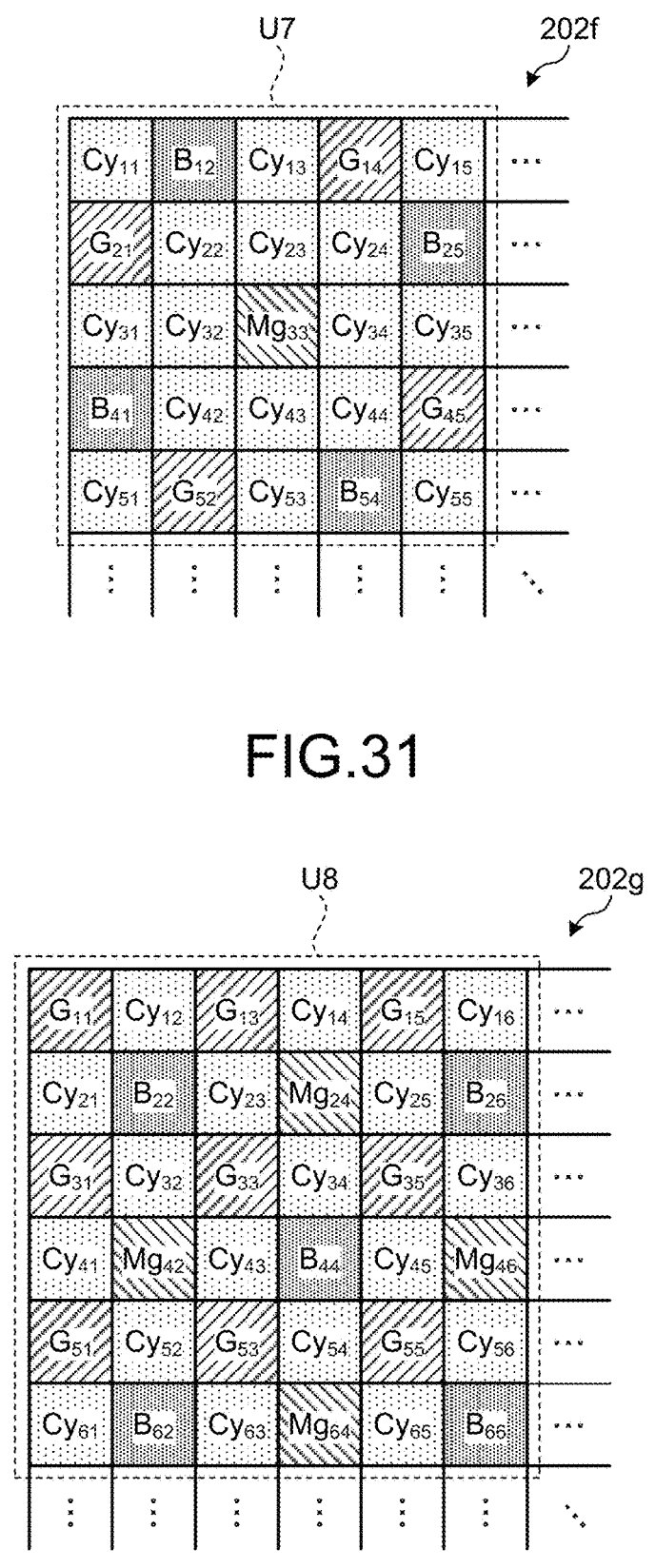

|     |     |     |     |     |     |
|-----|-----|-----|-----|-----|-----|
| $Cy_{11}$ | $B_{12}$ | $Cy_{13}$ | $G_{14}$ | $Cy_{15}$ | ... |
| $G_{21}$ | $Cy_{22}$ | $Cy_{23}$ | $Cy_{24}$ | $B_{25}$ | ... |
| $Cy_{31}$ | $Cy_{32}$ | $Mg_{33}$ | $Cy_{34}$ | $Cy_{35}$ | ... |
| $B_{41}$ | $Cy_{42}$ | $Cy_{43}$ | $Cy_{44}$ | $G_{45}$ | ... |
| $Cy_{51}$ | $G_{52}$ | $Cy_{53}$ | $B_{54}$ | $Cy_{55}$ | ... |
| ⋮ | ⋮ | ⋮ | ⋮ | ⋮ | ⋱ |

|     |     |     |     |     |     |     |
|-----|-----|-----|-----|-----|-----|-----|
| $G_{11}$ | $Cy_{12}$ | $G_{13}$ | $Cy_{14}$ | $G_{15}$ | $Cy_{16}$ | ... |
| $Cy_{21}$ | $B_{22}$ | $Cy_{23}$ | $Mg_{24}$ | $Cy_{25}$ | $B_{26}$ | ... |
| $G_{31}$ | $Cy_{32}$ | $G_{33}$ | $Cy_{34}$ | $G_{35}$ | $Cy_{36}$ | ... |
| $Cy_{41}$ | $Mg_{42}$ | $Cy_{43}$ | $B_{44}$ | $Cy_{45}$ | $Mg_{46}$ | ... |
| $G_{51}$ | $Cy_{52}$ | $G_{53}$ | $Cy_{54}$ | $G_{55}$ | $Cy_{56}$ | ... |
| $Cy_{61}$ | $B_{62}$ | $Cy_{63}$ | $Mg_{64}$ | $Cy_{65}$ | $B_{66}$ | ... |
| ⋮ | ⋮ | ⋮ | ⋮ | ⋮ | ⋮ | ⋱ |

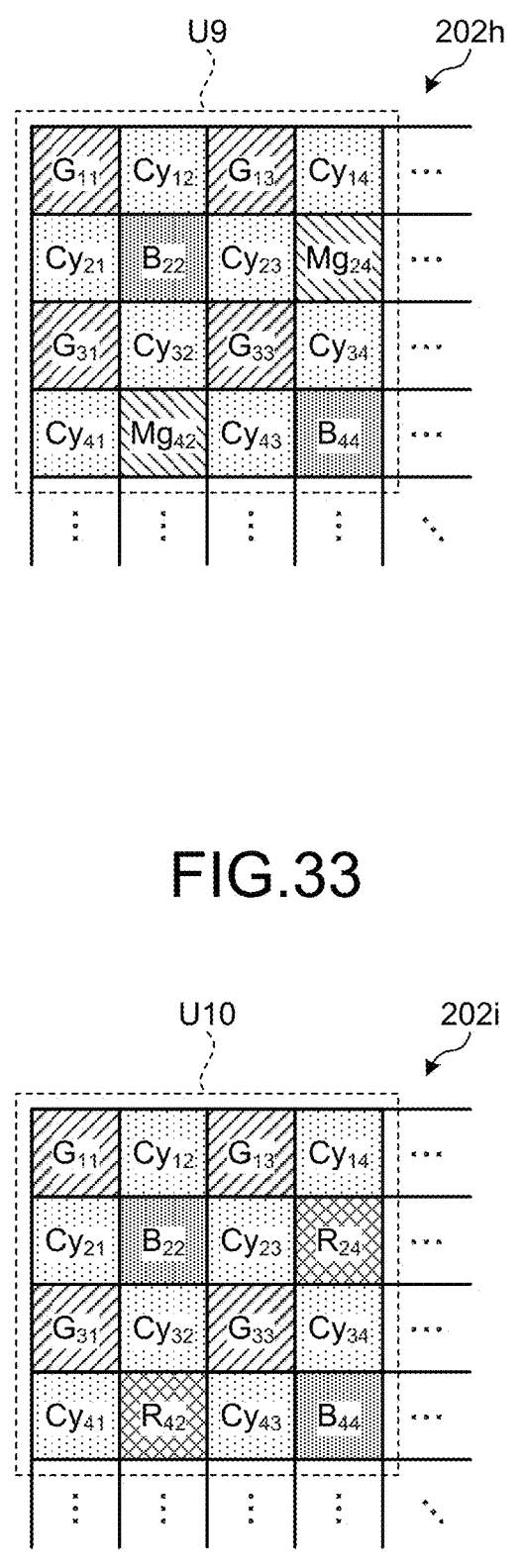

|  |  |  |  |  |
|---|---|---|---|---|
| $G_{11}$ | $Cy_{12}$ | $G_{13}$ | $Cy_{14}$ | ... |
| $Cy_{21}$ | $B_{22}$ | $Cy_{23}$ | $Mg_{24}$ | ... |
| $G_{31}$ | $Cy_{32}$ | $G_{33}$ | $Cy_{34}$ | ... |
| $Cy_{41}$ | $Mg_{42}$ | $Cy_{43}$ | $B_{44}$ | ... |

FIG.33

|  |  |  |  |  |
|---|---|---|---|---|
| $G_{11}$ | $Cy_{12}$ | $G_{13}$ | $Cy_{14}$ | ... |
| $Cy_{21}$ | $B_{22}$ | $Cy_{23}$ | $R_{24}$ | ... |
| $G_{31}$ | $Cy_{32}$ | $G_{33}$ | $Cy_{34}$ | ... |
| $Cy_{41}$ | $R_{42}$ | $Cy_{43}$ | $B_{44}$ | ... |

FIG.36

|  |  |  |  |
|---|---|---|---|
| $Cy_{11}$ | $G_{12}$ | $Cy_{13}$ | ... |
| $B_{21}$ | $Cy_{22}$ | $Mg_{23}$ | ... |
| $Cy_{31}$ | $G_{32}$ | $Cy_{33}$ | ... |
| ⋮ | ⋮ | ⋮ | ⋱ |

|  |  |  |  |  |  |
|---|---|---|---|---|---|
| $G_{11}$ | $Cy_{12}$ | $G_{13}$ | $Cy_{14}$ | $Mg_{15}$ | ... |
| $Cy_{21}$ | $B_{22}$ | $Cy_{23}$ | $B_{24}$ | $Cy_{25}$ | ... |
| $G_{31}$ | $Cy_{32}$ | $G_{33}$ | $Cy_{34}$ | $B_{35}$ | ... |
| $Cy_{41}$ | $B_{42}$ | $Cy_{43}$ | $Mg_{44}$ | $Cy_{45}$ | ... |
| $Mg_{51}$ | $Cy_{52}$ | $G_{53}$ | $Cy_{54}$ | $B_{55}$ | ... |
| ⋮ | ⋮ | ⋮ | ⋮ | ⋮ | ⋱ |

U14, 202m

ENDOSCOPE DEVICE, IMAGE PROCESSING APPARATUS, IMAGE PROCESSING METHOD, AND PROGRAM

CROSS-REFERENCE TO RELATED APPLICATION

This application is a continuation of International Application No. PCT/JP2017/005175, filed on Feb. 13, 2017, and which claims the benefit of priority from International Application No. PCT/JP2016/058002, filed on Mar. 14, 2016, the entire contents of which are incorporated herein by reference.

BACKGROUND OF THE INVENTION

1. Field of the Invention

The present disclosure relates to an endoscope device configured to be introduced into a subject and acquire an image inside the subject, and relates to an image processing apparatus, an image processing method, and a non-transitory computer readable storage medium.

2. Description of the Related Art

In the related art, endoscope devices have been widely used for various examinations in the medical field and the industrial field. Among them, medical endoscope devices can acquire in-vivo images inside a body cavity of a subject, such as a patient, without incision in the subject by introducing a long and thin flexible insertion portion that has a distal end portion in which an imaging device including a plurality of pixels is provided, and therefore, the medical endoscope devices are becoming popular because they can reduce load on the subject.

As observation methods for the endoscope devices as described above, white light imaging (WLI) using white illumination light (white light) and narrow band imaging (NBI) using illumination light (narrow band light) formed of two kinds of narrow band light included in a blue wavelength band and a green wavelength band are widely known. In the white light imaging, a color image is generated using a signal of the green wavelength band as a luminance signal, and, in the narrow band imaging, a pseudo color image is generated using a signal of the blue wavelength band as a luminance signal. In the narrow band imaging, it is possible to obtain an image in which capillaries, fine mucosal patterns, or the like that are present on a mucosal surface of a living body are displayed in an enhanced manner. With the narrow band imaging, it is possible to precisely detect a lesion site on the mucosal surface of the living body. With regard to the observation methods for the endoscope devices as described above, it is also known to conduct observations by switching between the white light imaging and the narrow band imaging.

To generate and display a color image using the observation methods as described above, a color filter called Bayer arrangement is generally provided on a light receiving surface of an imaging device in order to obtain a captured image by a single-chip imaging device. In the Bayer arrangement, each of filters that transmit light of a red (R) wavelength band, light of a green (G) wavelength band, and light of a blue (B) wavelength band (hereinafter, referred to as an "R filter", a "G filter", and a "B filter") is arranged for each of the pixels, as a single filter unit (unit). In this case, each of the pixels receives light of a wavelength band that has transmitted through the filter, and the imaging device generates an electrical signal of a color component corresponding to the light of the wavelength band. In a process of generating a color image using the electrical signal, an interpolation process is performed to interpolate signal values of color components that have been lost without transmission through the filter at each of the pixels. This interpolation process is referred to as a demosaicing process.

With regard to the demosaicing process, it is possible in the white light imaging to obtain high resolution in the green wavelength band by using, as luminance signals, signal values of pixels that receive light that has transmitted through the G filters, but, even when the same process as in the white light imaging is performed, it is difficult in the narrow band imaging to obtain an image with high resolution in the blue wavelength band that is used as luminance signals because a correlation between the G filter and the B filter is low and the B filters account for only one-fourth of the total filters in the arrangement. To solve this disadvantage, there is a known technique for interchanging positions of the G filters and positions of the B filters in the Bayer arrangement in order that the B filters are most frequently arranged in a single filter unit (see Japanese Laid-open Patent Publication No. 2006-297093 A).

SUMMARY OF THE INVENTION

However, in the above publication, while it is possible in the narrow band imaging to obtain an image with higher resolution in the blue wavelength band, which is used as the luminance signals, as compared to an image obtained using the Bayer arrangement, it is disadvantageous in that, in the white light imaging, resolution in the green wavelength band used as the luminance signals is reduced as compared to an image obtained using the conventional Bayer arrangement because the number of the G filters is smaller than that of the conventional Bayer arrangement.

The present disclosure has been conceived in view of the foregoing, and is directed to an improvement to an endoscope device, an image processing apparatus, an image processing method, and a non-transitory computer readable storage medium storing a program capable of obtaining an image with high resolution in both observation methods of white light imaging and narrow band imaging.

According to a first aspect of the present disclosure, there is provided an endoscope device including a light source, an imaging sensor, a color filter, and a processor. The light source is configured to emit first illumination light or second illumination light, the first illumination light including light of a red wavelength band, light of a green wavelength band, and light of a blue wavelength band, and the second illumination light including light of the green wavelength band and one of light of the blue wavelength band and light of the red wavelength band. The an imaging sensor includes a plurality of pixels that are arranged in a two-dimensional matrix and configured to receive light, perform photoelectric conversion on the light, and generate imaging signals. The color filter is configured such that a plurality of filter units are arranged so as to correspond to the plurality of pixels, each of the filter units including a plurality of filters including a first filter and a second filter such that the number of the second filters is equal to or larger than the number of the first filters that are most frequently arranged, the first filter being configured to transmit at least one of light of the red wavelength band, light of the green wavelength band, and light of the blue wavelength band, and the second filter being configured to transmit light of the green wavelength band and one of light of the red wavelength band and light of the blue wavelength band. The processor is formed of hardware and configured to generate a first image corresponding to light of the green wavelength band and a second image corresponding to light of one of the other wavelength bands on the basis of an imaging signal generated by the imaging device when the light source unit emits one of the first illumination light and the second illumination light. In the endoscope device according to the first aspect, resolution of the first image that is obtained when the light source unit emits the first illumination light is equal to or higher than resolution of the first image that is obtained when the light source unit emits the second illumination light, and resolution of the second image that is obtained when the light source unit emits the second illumination light is higher than resolution of the second image that is obtained when the light source unit emits the first illumination light.

According to a second aspect of the present disclosure, there is provided an image processing apparatus connected to an endoscope provided with a light source, an imaging sensor, a color filter, and a processor. The light source is configured to emit first illumination light or second illumination light, the first illumination light including light of a red wavelength band, light of a green wavelength band, and light of a blue wavelength band, and the second illumination light including light of the green wavelength band and one of light of the blue wavelength band and light of the red wavelength band. The imaging sensor includes a plurality of pixels that are arranged in a two-dimensional matrix and configured to receive light, perform photoelectric conversion on the light, and generate imaging signals. The color filter is configured such that a plurality of filter units are arranged so as to correspond to the plurality of pixels, each of the filter units including a plurality of filters including a first filter and a second filter such that the number of the second filters is equal to or larger than the number of the first filters that are most frequently arranged, the first filter being configured to transmit at least one of light of the red wavelength band, light of the green wavelength band, and light of the blue wavelength band, and the second filter being configured to transmit light of the green wavelength band and one of light of the red wavelength band and light of the blue wavelength band. The image processing apparatus includes a processor that is formed of hardware and configured to generate a first image corresponding to light of the green wavelength band and a second image corresponding to light of one of the other wavelength bands on the basis of an imaging signal generated by the imaging device when the light source unit emits one of the first illumination light and the second illumination light, wherein resolution of the first image that is obtained when the light source unit emits the first illumination light is equal to or higher than resolution of the first image that is obtained when the light source unit emits the second illumination light, and resolution of the second image that is obtained when the light source unit emits the second illumination light is higher than resolution of the second image that is obtained when the light source unit emits the first illumination light.

According to a third aspect of the present disclosure, there is provided an image processing method performed by an image processing apparatus connected to an endoscope provided with a light source, an imaging sensor, and a color filter. The light source is configured to emit first illumination light or second illumination light, the first illumination light including light of a red wavelength band, light of a green wavelength band, and light of a blue wavelength band, and the second illumination light including light of the green wavelength band and one of light of the blue wavelength band and light of the red wavelength band. The imaging sensor includes a plurality of pixels that are arranged in a two-dimensional matrix and configured to receive light, perform photoelectric conversion on the light, and generate imaging signals. The color filter is configured such that a plurality of filter units are arranged so as to correspond to the plurality of pixels, each of the filter units including a plurality of filters including a first filter and a second filter such that the number of the second filters is equal to or larger than the number of the first filters that are most frequently arranged, the first filter being configured to transmit at least one of light of the red wavelength band, light of the green wavelength band, and light of the blue wavelength band, and the second filter being configured to transmit light of the green wavelength band and one of light of the red wavelength band and light of the blue wavelength band.

The image processing method includes generating a first image corresponding to light of the green wavelength band and a second image corresponding to light of one of the other wavelength bands on the basis of an imaging signal generated by the imaging device when the light source unit emits one of the first illumination light and the second illumination light, wherein resolution of the first image that is obtained when the light source unit emits the first illumination light is equal to or higher than resolution of the first image that is obtained when the light source unit emits the second illumination light, and resolution of the second image that is obtained when the light source unit emits the second illumination light is higher than resolution of the second image that is obtained when the light source unit emits the first illumination light.

According to a fourth aspect of the present disclosure, there is provided a non-transitory computer readable storage medium storing a program that causes an image processing apparatus connected to an endoscope provided with a light source, an imaging sensor, and a color filter. The light source configured to emit first illumination light or second illumination light, the first illumination light including light of a red wavelength band, light of a green wavelength band, and light of a blue wavelength band, and the second illumination light including light of the green wavelength band and one of light of the blue wavelength band and light of the red wavelength band. The an imaging sensor including a plurality of pixels that are arranged in a two-dimensional matrix and configured to receive light, perform photoelectric conversion on the light, and generate imaging signals. The a color filter configured such that a plurality of filter units are arranged so as to correspond to the plurality of pixels, each of the filter units including a plurality of filters including a first filter and a second filter such that the number of the second filters is equal to or larger than the number of the first filters that are most frequently arranged, the first filter being configured to transmit at least one of light of the red wavelength band, light of the green wavelength band, and light of the blue wavelength band, and the second filter being configured to transmit light of the green wavelength band and one of light of the red wavelength band and light of the blue wavelength band. The program causes the image processing apparatus to execute generating a first image corresponding to light of the green wavelength band and a second image corresponding to light of one of the other wavelength bands on the basis of an imaging signal generated by the imaging device when the light source unit emits one of the first illumination light and the second illumination light, wherein resolution of the first image that is obtained when the light source unit emits the first illumination light is equal

BRIEF DESCRIPTION OF THE DRAWINGS

FIG. 29 is a diagram illustrating a list, in which variations of color filters, wavelength bands of illumination light emitted by a light source unit, and results are associated with one another, according to another embodiment of the present disclosure;

FIG. 30 is a diagram illustrating an example of a configuration of a color filter according to still another embodiment of the present disclosure;

FIG. 31 is a diagram illustrating an example of a configuration of a color filter according to still another embodiment of the present disclosure;

FIG. 32 is a diagram illustrating an example of a configuration of a color filter according to still another embodiment of the present disclosure;

FIG. 33 is a configuration of a color filter according to still another embodiment of the present disclosure;

FIG. 36 is a configuration of a color filter according to still another embodiment of the present disclosure;

FIG. 37 is a configuration of a color filter according to still another embodiment of the present disclosure;

DETAILED DESCRIPTION OF THE PREFERRED EMBODIMENTS

Hereinafter, modes for carrying out the present disclosure (hereinafter, referred to as "embodiments") will be described. In the embodiments, a medical endoscope device that captures an image inside a body cavity of a subject, such as a patient, and displays the image will be described. The present disclosure is not limited by the embodiments below. The same components will be denoted by the same reference signs throughout the drawings.

First Embodiment

Configuration of Endoscope Device

Figure 1:
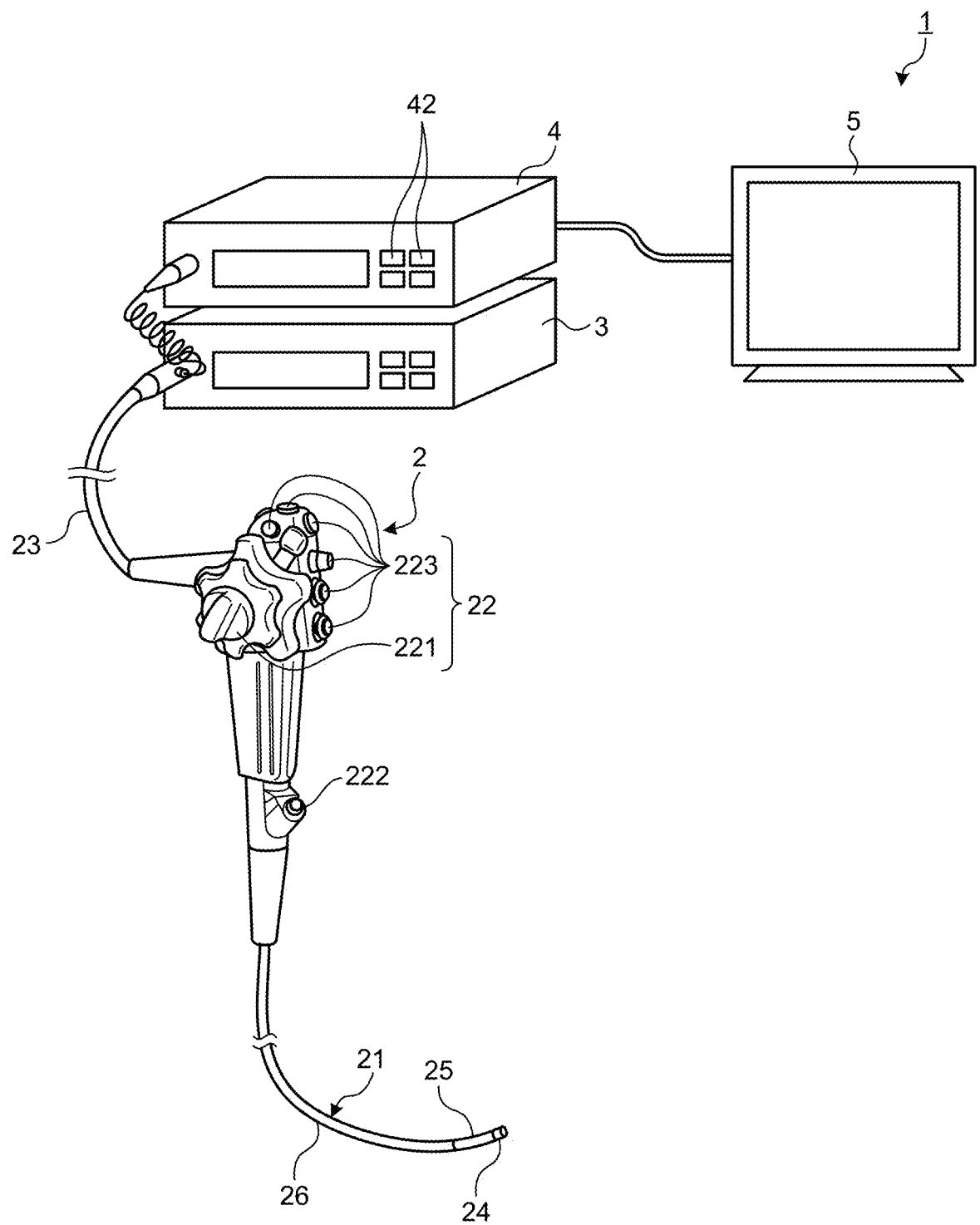
FIG. 1 is a diagram illustrating an overall configuration of an endoscope device according to a first embodiment of the present disclosure.
Figure 2:
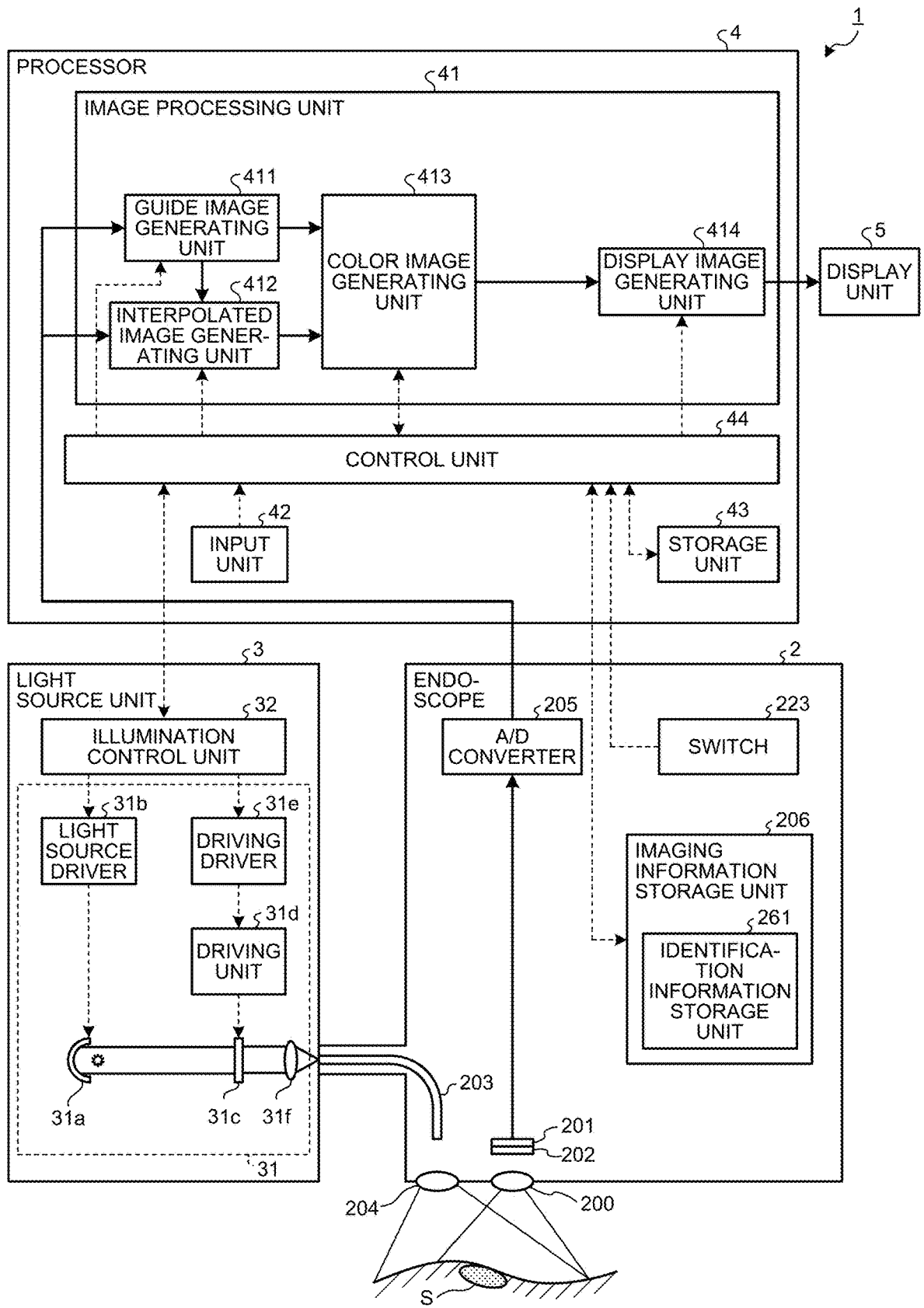
FIG. 2 is a schematic diagram illustrating an overall configuration of the endoscope device according to the first embodiment of the present disclosure.

FIG. 1 is a diagram illustrating an overall configuration of an endoscope device according to a first embodiment of the present disclosure. FIG. 2 is a schematic diagram illustrating an overall configuration of the endoscope device according to the first embodiment of the present disclosure. As illustrated in FIG. 1 and FIG. 2, an endoscope device 1 captures an image inside a subject, such as a patient, by introducing a distal end part of an endoscope into the subject, and displays the in-vivo image. A user, such as a doctor, observes the displayed in-vivo image, and examines presence or absence of a bleeding site, a tumor region (lesion site S), and an abnormal region in detection target regions.

The endoscope device 1 includes an endoscope 2 that captures an in-vivo image of an observed region and generates an electrical signal by being introduced into the subject, a light source unit 3 that generates illumination light to be emitted from a distal end of the endoscope 2, a processor 4 that performs predetermined image processing on the electrical signal generated by the endoscope 2 and comprehensively controls whole operation of the endoscope device 1, and a display unit 5 that displays the in-vivo image that is subjected to the image processing by the processor 4.

Configuration of Endoscope

First, a configuration of the endoscope 2 will be described. The endoscope 2 includes a long and thin flexible insertion portion 21, an operating unit 22 that is connected to a proximal end side of the insertion portion 21 and receives input of various operation signals. The endoscope 2 further includes a universal cord 23 that extends in a direction different from a direction in which the insertion portion 21 extends from the operating unit 22. The universal cord 23 houses various cables connected to the light source unit 3 and the processor 4.

The insertion portion 21 includes a tip portion 24, a bending portion 25, and an elongated flexible tube 26. The tip portion 24 that houses an imaging device 201 (FIG. 2) which includes pixels (photodiodes) that are arranged in a two-dimensional matrix and configured to receive light and generate image signals by performing photoelectric conversion on the received light. The bending portion 25 is constituted by a plurality of bending pieces and is freely bendable. The elongated flexible tube 26 is connected to a proximal end side of the bending portion 25 and has flexibility.

The operating unit 22 includes a bending knob 221 for bending the bending portion 25 in a vertical direction and a horizontal direction, a treatment tool insertion portion 222 for inserting a treatment tool, such as a biopsy forceps, an electric scalpel, or an inspection probe, into the body cavity of the subject, and a plurality of switches 223 for receiving input of an instruction signal for causing the light source unit 3 to perform illumination-light switching operation, or the like.

The universal cord 23 houses at least a light guide 203 and an assembly cable in which one or a plurality of signal lines are assembled. The assembly cable is a signal line that transmits and receives a signal between the endoscope 2, the light source unit 3, and the processor 4, and includes a signal line for transmitting and receiving setting data, a signal line for transmitting and receiving an image signal, a signal line for transmitting and receiving a driving timing signal for driving the imaging device 201, and the like.

Referring to FIG. 2, the endoscope 2 includes an imaging optical system 200, the imaging device 201, a color filter 202, the light guide 203, an illumination lens 204, an analog-to-digital (A/D) converter 205, and an imaging information storage unit 206.

The imaging optical system 200 is provided on the tip portion 24 of the insertion portion 21 (FIG. 1), and condenses at least light from an observed region. The imaging optical system 200 is constituted by one or more lenses. The imaging optical system 200 may include an optical zoom mechanism that changes an angle of view and a focus mechanism that changes a focal point.

The imaging device 201 is arranged perpendicular to an optical axis of the imaging optical system 200, and configured to receive light of a subject image formed on the imaging optical system 200, perform photoelectric conversion on the light to generate an electrical signal (image signal), and output the electrical signal to the A/D converter 205. The imaging device 201 is realized using an image sensor, such as a charge coupled device (CCD) or a complementary metal oxide semiconductor (CMOS). A detailed configuration of the imaging device 201 will be described later.

The color filter 202 is arranged on a light receiving surface of the imaging device 201, and includes a plurality of filters, each of which transmits light of a wavelength band that is set individually. A detailed configuration of the color filter 202 will be described later.

The light guide 203 is constituted by fiberglass or the like, and serves as an optical waveguide of light emitted by the light source unit 3.

The illumination lens 204 is provided on a distal end of the light guide 203, diffuses light guided by the light guide 203, and emits the light to the outside of the tip portion 24. The illumination lens 204 is constituted by one or more lenses.

The A/D converter 205 performs A/D conversion on an analog electrical signal generated by the imaging device 201, and outputs the converted digital electrical signal to the processor 4.

The imaging information storage unit 206 stores therein various programs for operating the endoscope 2, various parameters needed for operation of the endoscope 2, and data including identification information on the endoscope 2. Further, the imaging information storage unit 206 includes an identification information storage unit 261 for recording identification information. The identification information includes unique information (ID), a model year, specification information, a transmission system, information on arrangement of filters in the color filter 202, and the like, regarding the endoscope 2. The imaging information storage unit 206 is realized using a flash memory or the like.

Configuration of Light Source Unit

Next, a configuration of the light source unit 3 will be described. The light source unit 3 includes an illumination unit 31 and an illumination control unit 32.

The illumination unit 31 switches between a plurality of kinds of illumination light, and outputs the illumination light to the light guide 203 under the control of the illumination control unit 32. The illumination unit 31 includes a light source 31*a*, a light source driver 31*b*, a switching filter 31*c*, a driving unit 31*d*, and a driving driver 31*e*.

The light source 31*a* outputs white light including light of a red wavelength band $H_R$, light of a green wavelength band $H_G$, and light of a blue wavelength band $H_B$ in accordance with an electric current input from the light source driver 31*b*. The light source 31*a* is realized using a white light emitting diode (LED), a xenon lamp, or the like.

The light source driver 31*b* supplies an electric current to the light source 31*a* and causes the light source 31*a* to emit white light under the control of the illumination control unit 32.

The switching filter 31*c* is arranged so as to be freely placed into and removed from an optical path of the white light emitted by the light source 31*a*, and transmits light of a predetermined wavelength band in the white light emitted by the light source 31*a*. In the first embodiment, the switching filter 31*c* transmits blue narrow band light and green narrow band light. That is, in the first embodiment, when the switching filter 31*c* is placed into the optical path of the white light, the switching filter 31*c* transmits two kinds of narrow band light. Specifically, the switching filter 31*c* transmits light of a narrow band $T_B$ (for example, 390 nanometers (nm) to 445 nm) included in the wavelength band $H_B$, and light of a narrow band $T_G$ (for example, 530 nm to 550 nm) included in the wavelength band $H_G$. The light that has transmitted through the switching filter 31*c* serves as narrow-band illumination light of the narrow band $T_B$ and the narrow band $T_G$. The narrow bands $T_B$ and $T_G$ are wavelength bands of blue light and green light that are easily absorbed into hemoglobin in blood. Observation of an image using the narrow-band illumination light is referred to as narrow band imaging (NBT).

The driving unit 31*d* is constituted by a stepping motor, a DC motor, or the like, and causes the switching filter 31*c* to be placed into or removed from the optical path of the white light emitted by the light source 31*a*, under the control of the illumination control unit 32. Specifically, when the endoscope device 1 performs white light imaging (WLI system) with light as first illumination light, the driving unit 31*d* causes the switching filter 31*c* to be removed from the optical path of the white light emitted by the light source 31*a*, under the control of the illumination control unit 32. When the endoscope device 1 performs narrow band imaging (NBI system) with light as second illumination light, the driving unit 31*d* causes the switching filter 31*c* to be placed into the optical path of the white light emitted by the light source 31*a*, under the control of the illumination control unit 32.

The driving driver 31*e* supplies a predetermined electric current to the driving unit 31*d* under the control of the illumination control unit 32.

A condenser lens 31*f* condenses the white light emitted by the light source 31*a* and outputs the white light to the light guide 203. Further, the condenser lens 31*f* condenses light that has transmitted through the switching filter 31*c* and outputs the light to the light guide 203. The condenser lens 31*f* is constituted by one or more lenses.

The illumination control unit 32 is constituted by a central processing unit (CPU) or the like. The illumination control unit 32 controls the light source driver 31*b* so as to turn on and off the light source 31*a* based on an instruction signal input from the processor 4. Further, the illumination control unit 32 controls the driving driver 31*e* so as to cause the switching filter 31*c* to be placed into and removed from the optical path of the white light emitted by the light source 31*a* based on an instruction signal input from the processor 4, to thereby control types of illumination light to be emitted by the illumination unit 31.

Configuration of Processor

Next, a configuration of the processor 4 will be described with reference to FIG. 4. The processor 4 includes an image processing unit 41, an input unit 42, a storage unit 43, and a control unit 44.

The image processing unit 41 performs predetermined image processing on an electrical signal input from the endoscope 2 and generates a display image to be displayed by the display unit 5. Specifically, when the light source unit 3 emits white light (first illumination light) or narrow band light (second illumination light), the image processing unit 41 generates a first image corresponding to light of a green wavelength band and a second image corresponding to light of one of the other wavelength bands (in the first embodiment, light of a blue wavelength band) on the basis of an imaging signal generated by the imaging device 201. Here, resolution of the first image that is obtained when the light source unit 3 emits the white light is equal to or higher than resolution of the first image that is obtained when the light source unit 3 emits the narrow band light. Further, resolution of the second image that is obtained when the light source unit 3 emits the narrow band light is higher than resolution of the second image that is obtained when the light source unit 3 emits the white light. The image processing unit 41 includes a guide image generating unit 411, an interpolated image generating unit 412, a color image generating unit 413, and a display image generating unit 414.

The guide image generating unit 411 generates, based on an electrical signal input from the endoscope 2, a guide image to be used as a guide for interpolating electrical signals of other pixels when the interpolated image generating unit 412 performs an interpolation process, and outputs the guide image to the interpolated image generating unit 412 and the color image generating unit 413. In the first embodiment, the guide image functions as a first interpolated image.

The interpolated image generating unit 412 generates an interpolated image by performing an interpolation process on the electrical signal input from the endoscope 2 on the basis of the guide image input from the guide image generating unit 411, and outputs the interpolated image (second interpolated image) to the color image generating unit 413.

The color image generating unit 413 generates a color image using the interpolated image input from the interpolated image generating unit 412 on the basis of the guide image input from the guide image generating unit 411, and outputs the color image to the display image generating unit 414.

The display image generating unit 414 performs tone conversion, an enlargement process, or a structure enhancement process for structures, such as capillaries or fine mucosal patterns on a mucosal surface, on the electrical signal generated by the color image generating unit 413. After performing predetermined processing, the display image generating unit 414 outputs, to the display unit 5, the signal as a display image signal used for displaying.

The input unit 42 is an interface for performing input to the processor 4 from a user for example, and includes a power switch for turning on and off the power supply, a mode switching button for switching between imaging modes and various other modes, and an illumination light switching button for switching between types of illumination light of the light source unit 3.

The storage unit 43 stores therein various programs for operating the endoscope device 1 and data including various parameters or the like needed for operation of the endoscope device 1. Further, the storage unit 43 may store therein a relation table containing information on the endoscope 2, such as the unique information (ID) on the endoscope 2 and the information on arrangement of the filters in the color filter 202. The storage unit 43 is realized using a semiconductor memory, such as a flash memory or a dynamic random access memory (DRAM).

The control unit 44 is constituted by a CPU or the like, and performs drive control on each of the components including the endoscope 2 and the light source unit 3, input-output control on information with respect to each of the components, and the like. The control unit 44 transmits setting data for imaging control (for example, a read target pixel or the like), a timing signal related to an imaging timing, and the like, which are recorded in the storage unit 43, to the endoscope 2 via a predetermined signal line. The control unit 44 outputs color filter information (identification information), which is acquired via the imaging information storage unit 206, to the image processing unit 41, and outputs information related to arrangement of the switching filter 31c to the light source unit 3 on the basis of the color filter information.

Configuration of Display Unit

Next, the display unit 5 (FIG. 1) will be described. The display unit 5 receives the display image signal generated by the processor 4 via a video cable, and displays an in-vivo image corresponding to the display image signal. The display unit 5 is constituted by liquid crystal or organic electroluminescence (EL).

Configuration of Imaging Device

Figure 3:
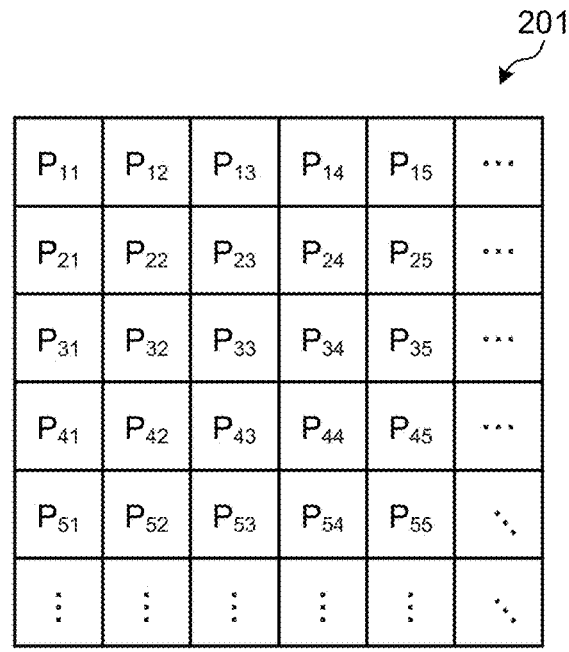
FIG. 3 is a schematic diagram illustrating a configuration of pixels of an imaging device according to the first embodiment of the present disclosure.

Next, a detailed configuration of the imaging device 201 will be described. FIG. 3 is a schematic diagram illustrating a configuration of pixels of the imaging device 201.

As illustrated in FIG. 3, the imaging device 201 includes a plurality of pixels P that are arranged in a two-dimensional grid pattern (two-dimensional matrix array) and configured to receive light from the imaging optical system 200. Each of the pixels P receives light incident from the imaging optical system 200, performs photoelectric conversion on the light, and generates an electrical signal. The electrical signal includes a luminance value (pixel value) of each of the pixels P, positional information on the pixel, and the like. In FIG. 3, a pixel arranged in the i-th row and the j-th column will be referred to as a pixel $P_{ij}$. i and j are integers equal to or greater than one.

Configuration of Color Filter

Next, a detailed configuration of the color filter 202 will be described. FIG. 4 is a schematic diagram illustrating an example of the configuration of the color filter 202.

Figure 4:
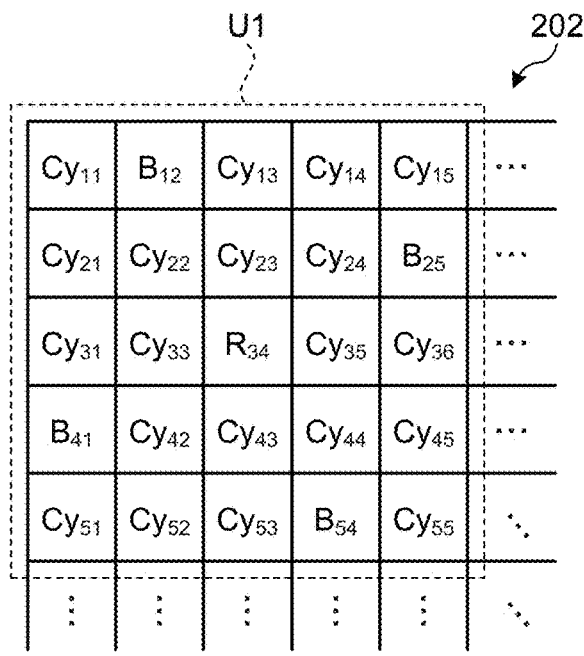
FIG. 4 is a schematic diagram illustrating an example of a configuration of a color filter according to the first embodiment of the present disclosure.

As illustrated in FIG. 4, the color filter 202 is configured such that filter units U1, each of which includes 25 filters arranged in a two-dimensional 5×5 matrix, are arranged in accordance with arrangement of the pixels $P_{ij}$. The pixel $P_{ij}$ provided with a certain filter receives light of a wavelength band that has transmitted through the filter. Specifically, the pixel $P_{ij}$ provided with a filter that transmits light of a red wavelength band receives light of the red wavelength band. Hereinafter, the pixel $P_{ij}$ that receives light of the red wavelength band is referred to as an R pixel. Similarly, the pixel $P_{ij}$ that receives light of the green wavelength band is referred to as a G pixel, pixel $P_{ij}$ that receives light of the blue wavelength band is referred to as a B pixel, and the pixel $P_{ij}$ that receives light of the green wavelength band and light of the blue wavelength band is referred to as a Cy pixel.

As illustrated in FIG. 4, the filter unit U1 transmits light of the blue (B) wavelength band $H_B$, light of the green (G) wavelength band $H_G$, and light of the red (R) wavelength band $H_R$. Here, the blue wavelength band $H_B$, the green wavelength band $H_G$, and the red wavelength band $H_R$ are defined such that the wavelength band $H_B$ is 390 nm to 500 nm, the wavelength band $H_G$ is 500 nm to 600 nm, and the wavelength band $H_R$ is 600 nm to 700 nm. Further, the filter unit U1 includes R filters that transmit light of the red wavelength band $H_R$, B filters that transmit light of the blue wavelength band, and Cy filters that transmit light of the blue wavelength band and light of the green wavelength band. Specifically, the filter unit U1 includes one R filter, four B filters, and 20 Cy filters. Further, the filter unit U1 is configured such that the number of the Cy filters is equal to or larger than the number of the B filters that are most frequently arranged in the color filter 202 among a plurality of types of first filters (described below). Specifically, a ratio between the number of the Cy filters and the number of the B filters is 5:1. Further, the Cy filters are arranged at all of adjacent positions of the R filter. Hereinafter, when the B filter is arranged at a position corresponding to the pixel $P_{ij}$, the B filter is denoted by $B_{ij}$. Similarly, when the R filter is arranged at a position corresponding to the pixel $P_{ij}$, the R filter is denoted by $R_{ij}$, and when the Cy filter is arranged at a position corresponding to the pixel $P_{ij}$, the Cy filter is denoted by $Cy_{ij}$. In the first embodiment, the B filter and the R filter function as the first filters, and the Cy filter functions as a second filter.

Transmission Characteristic of Each Filter

Figure 5:
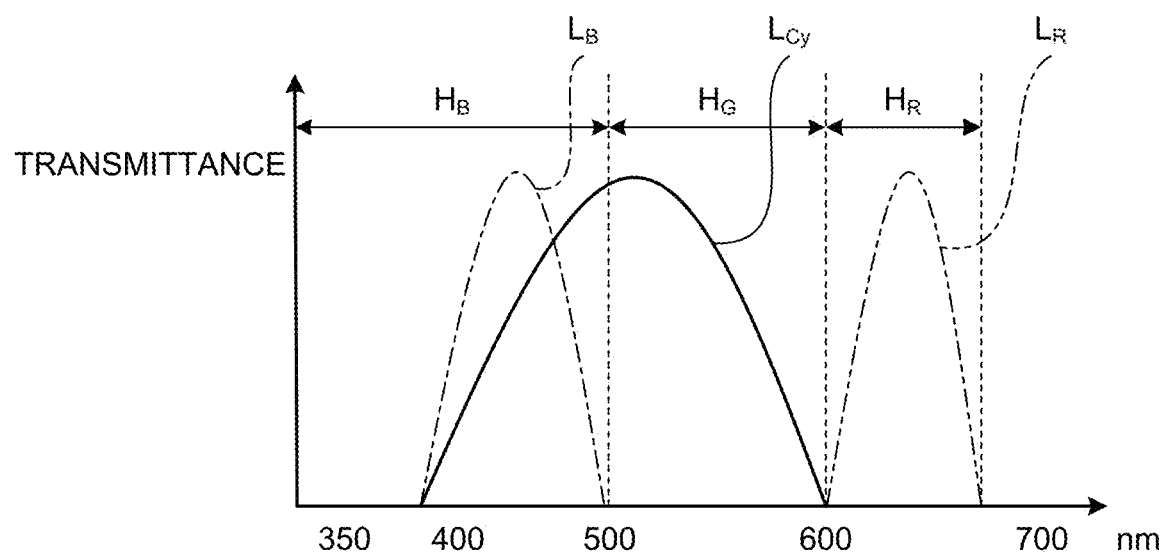
FIG. 5 is a diagram illustrating an example of a transmission characteristic of each of filters included in the color filter according to the first embodiment of the present disclosure.

Next, a transmission characteristic of each of the filters included in the color filter 202 will be described. FIG. 5 is a diagram illustrating an example of the transmission characteristic of each of the filters included in the color filter 202. In FIG. 5, transmittance curves are standardized in a simulative manner such that maximum values of transmittances of all of the filters are equalized. In FIG. 5, a curved line $L_B$ represents a transmittance curve of the B filter, a curved line $L_R$ represents a transmittance curve of the R filter, and a curved line $L_{Cy}$ represents a transmittance curve of the Cy filter. Further, in FIG. 5, a horizontal axis represents a wavelength and a vertical axis represents a transmittance.

As illustrated in FIG. 5, the B filter transmits light of the wavelength band $H_B$. The Cy filter transmits light of the wavelength band $H_B$ and light of the wavelength band $H_G$, and absorbs (blocks) light of the wavelength band $H_R$. That is, the Cy filter transmits light of a cyan wavelength band, where the cyan is a complementary color. The R filter transmits light of the wavelength band $H_R$. In the present specification, the complementary color indicates a color configured with light of at least two of the wavelength bands $H_B$, $H_G$, and $H_R$.

Spectral Characteristic of Light Source Unit

Figure 6:
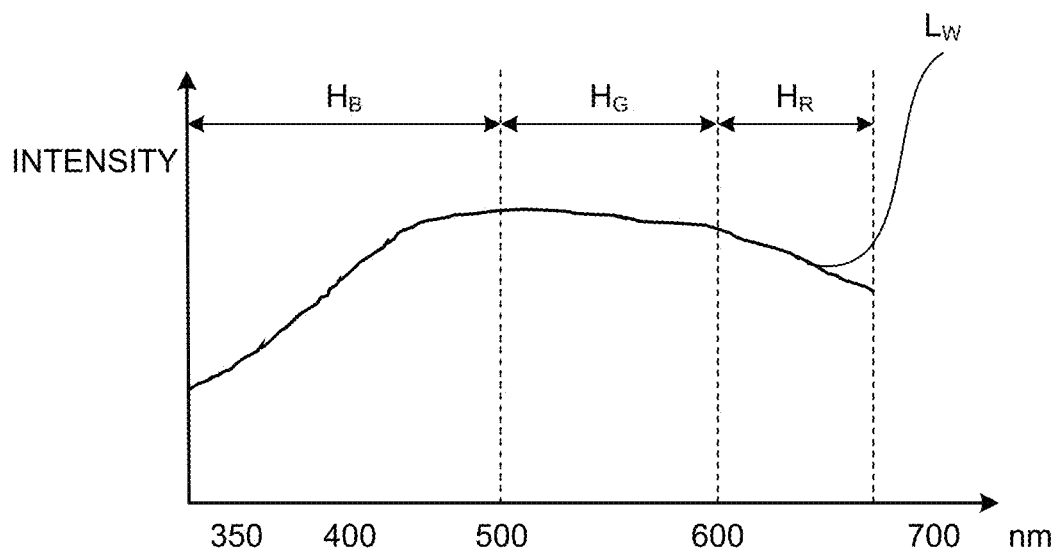
FIG. 6 is a diagram illustrating an example of a spectral characteristic of white light emitted by a light source unit according to the first embodiment of the present disclosure.
Figure 7:
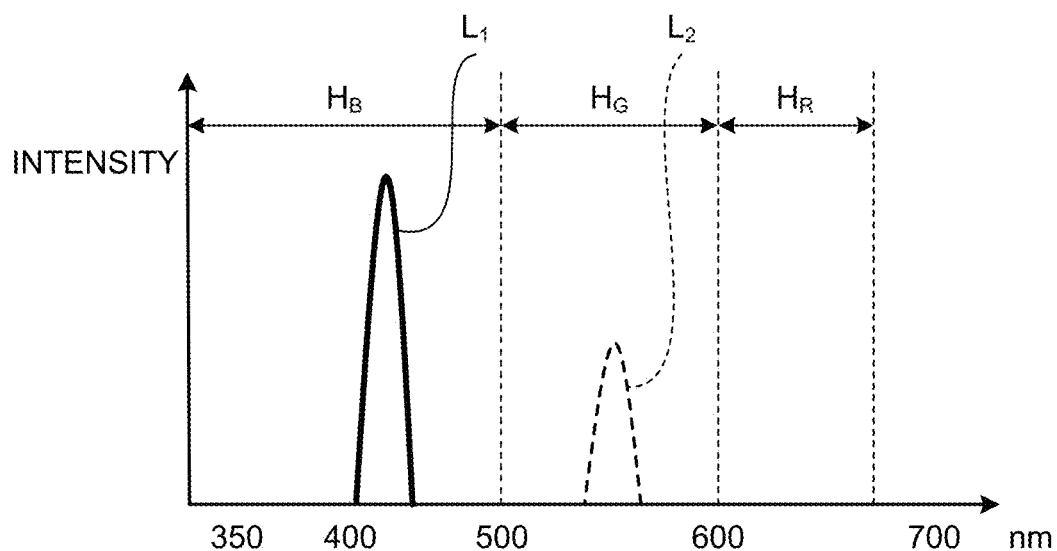
FIG. 7 is a diagram illustrating an example of a spectral characteristic of narrow band light emitted by the light source unit according to the first embodiment of the present disclosure.

Next, a spectral characteristic of light emitted by the light source unit 3 will be described. FIG. 6 is a diagram illustrating an example of a spectral characteristic of white light emitted by the light source unit 3. FIG. 7 is a diagram illustrating an example of a spectral characteristic of narrow band light emitted by the light source unit 3. In FIG. 6 and FIG. 7, horizontal axes represent a wavelength and vertical axes represent intensity. In FIG. 6, a curved line $L_W$ represents the spectral characteristic of the white light emitted by the light source unit 3. Further, in FIG. 7, a curved line $L_1$ and a curved line $L_2$ represent the spectral characteristic of the narrow band light emitted by the light source unit 3.

As indicated by the curved line $L_W$ in FIG. 6, the white light emitted by the light source unit 3 has higher intensity in the green wavelength band $H_G$ than intensity in the blue wavelength band $H_B$. Further, as indicated by the curved line $L_1$ and the curved line $L_2$ in FIG. 7, the narrow band light emitted by the light source unit 3 has higher intensity in the blue wavelength band $H_B$ than intensity in the green wavelength band $H_G$. In this manner, light received by each of the pixels $P_{ij}$ is information that is a hybrid of the spectral characteristic of light emitted by the light source unit 3 and the transmission characteristic of each of the filters. That is, when emitting the white light as the first illumination light, the light source unit 3 emits light of the green wavelength band $H_G$ with higher intensity than light of the blue wavelength band $H_B$, and, when emitting the narrow band light as the second illumination light, the light source unit 3 emits light of the blue wavelength band $H_B$ with higher intensity than light of the green wavelength band $H_G$. In the present embodiment, the intensity of the wavelength band is not peak intensity, but an integral value in the wavelength band.

Relationship Between Each Light and Cy Filter

Figure 8:
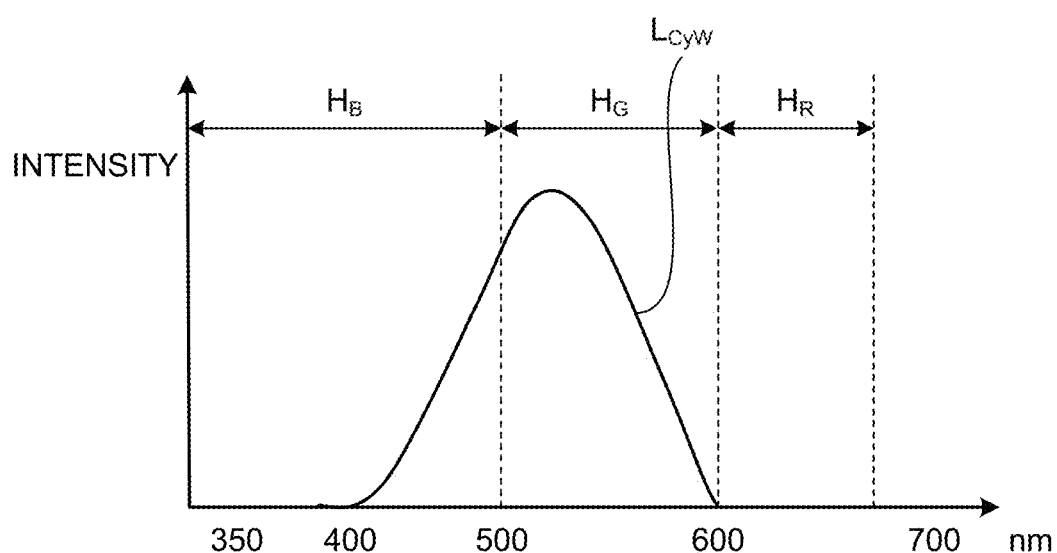
FIG. 8 is a diagram illustrating an example of a transmission characteristic of a Cy filter in a case where the light source unit according to the first embodiment of the present disclosure emits white light toward the Cy filter.
Figure 9:
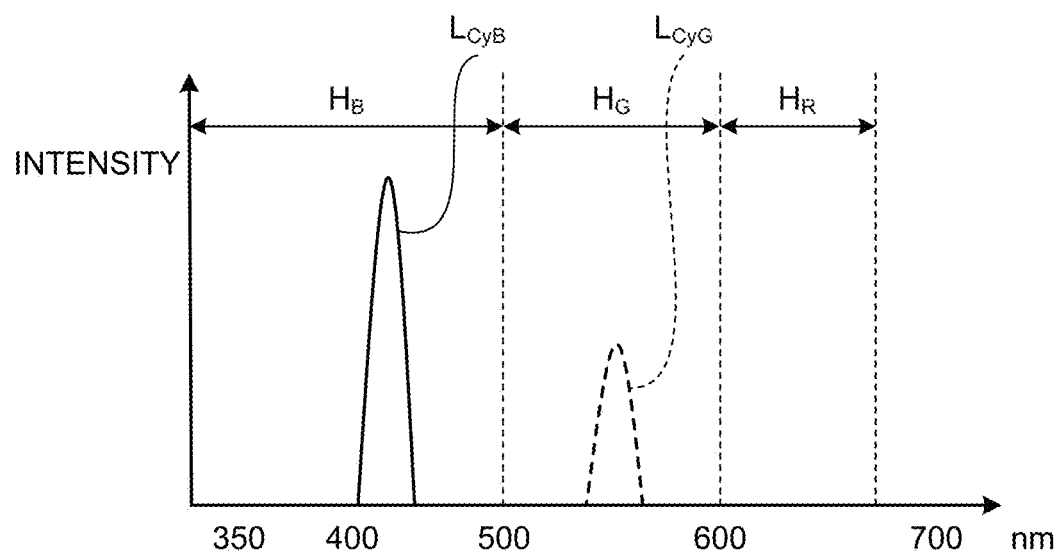
FIG. 9 is a diagram illustrating an example of a transmission characteristic of the Cy filter in a case where the light source unit according to the first embodiment of the present disclosure emits narrow band light toward the Cy filter.

Next, a transmission characteristic of the Cy filter in a case where the light source unit 3 emits each light toward the Cy filter will be described. FIG. 8 is a diagram illustrating an example of a transmission characteristic of the Cy filter in a case where the light source unit 3 emits the white light toward the Cy filter. FIG. 9 is a diagram illustrating an example of a transmission characteristic of the Cy filter in a case where the light source unit 3 emits the narrow band light toward the Cy filter. In FIG. 8 and FIG. 9, horizontal axes represent a wavelength and vertical axes represent intensity. In FIG. 8, a curved line $L_{CyW}$ represents the transmission characteristic of the Cy filter in a case where the light source unit 3 emits the white light toward the Cy filter. Further, in FIG. 9, a curved line $L_{CyB}$ and a curved line $L_{CyG}$ represent the transmission characteristic of the Cy filter in a case where the light source unit 3 emits the narrow band light toward the Cy filter.

As indicated by the curved line $L_{CyW}$ in FIG. 8, the Cy filter has a characteristic that, when the light source unit 3 emits the white light toward the Cy filter, a transmittance of the green wavelength band $H_G$ is higher than a transmittance of the blue wavelength band $H_B$ and light of the green wavelength band $H_G$ is relatively largely transmitted. That is, a $Cy_{ij}$ pixel acquires a larger amount of information on the green wavelength band $H_G$ than information on the blue wavelength band $H_B$.

In contrast, as indicated by a curved line $L_{CyB}$ and a curved line $L_{CyG}$ in FIG. 9, the Cy filter has a characteristic that, when the light source unit 3 emits the narrow band light toward the Cy filter, the transmittance of the blue wavelength band $H_B$ is higher than the transmittance of the green wavelength band $H_G$ and light of the blue wavelength band $H_B$ is relatively largely transmitted. That is, the $Cy_{ij}$ pixel acquires a larger amount of information on the blue wavelength band $H_B$ than information on the green wavelength band $H_G$.

Information Acquired by Cy Pixel

Next, information acquired by the Cy pixel will be described. FIG. 10A to FIG. 10E are diagrams illustrating examples of an image obtained when the Cy filter is arranged on a light receiving surface of each of the pixels $P_{ij}$.

Figure 10A:
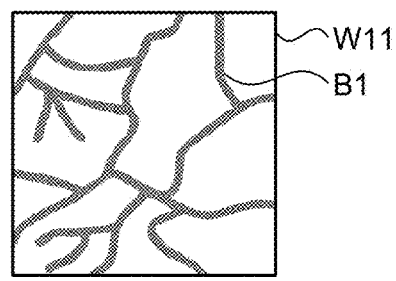
FIG. 10A is a diagram illustrating an example of an image obtained when the Cy filter is arranged on a light receiving surface of each pixel.
Figure 10B:
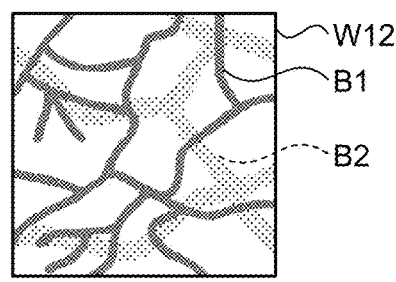
FIG. 10B is a diagram illustrating an example of an image obtained when the Cy filter is arranged on the light receiving surface of each pixel.
Figure 10C:
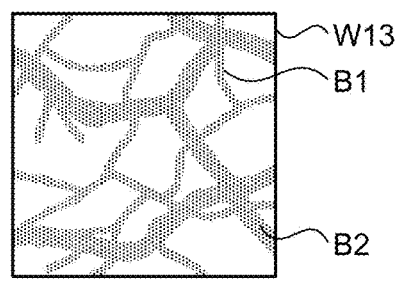
FIG. 10C is a diagram illustrating an example of an image obtained when the Cy filter is arranged on the light receiving surface of each pixel.
Figure 10D:
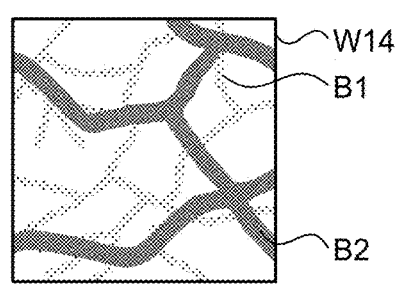
FIG. 10D is a diagram illustrating an example of an image obtained when the Cy filter is arranged on the light receiving surface of each pixel.
Figure 10E:
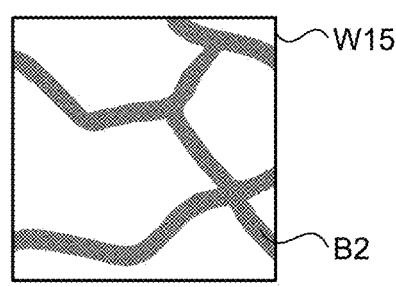
FIG. 10E is a diagram illustrating an example of an image obtained when the Cy filter is arranged on the light receiving surface of each pixel.

The Cy pixel has sensitivity to each of the blue wavelength band $H_B$ and the green wavelength band $H_G$. Therefore, the Cy pixel can acquire information in which information on a capillary B1 on a surface, which is information on the blue wavelength band $H_B$ (see FIG. 10A), and information on a thick blood vessel B2, which is information on the green wavelength band $H_G$ (see FIG. 10E), are mixed. When a ratio between the blue wavelength band $H_B$ and the green wavelength band $H_G$ is 1:1 in the sensitivity characteristic including light emitted by the light source unit 3 as illustrated in FIG. 8 and FIG. 9, the Cy pixel acquires an image W13 as illustrated in FIG. 10C, which is information in which an image W11 illustrated in FIG. 10A and an image W15 illustrated in FIG. 10E are averaged. In contrast, when the ratio between the blue wavelength band $H_B$ and the green wavelength band $H_G$ is changed, the Cy pixel can acquire information on an image, such as an image W12 as illustrated in FIG. 10B or an image W14 as illustrated in FIG. 10D.

The Cy pixels are most frequently arranged in the imaging device 201. Therefore, when the light source unit 3 emits the second illumination light (narrow band light), the Cy pixels can acquire a large amount of information on the blue wavelength band $H_B$, which is obtainable from the Cy pixels. That is, when the light source unit 3 emits the second illumination light, the second image generated by the image processing unit 41 is a sum of information on the blue wavelength band $H_B$ obtained from the Cy pixels and information on the blue wavelength band $H_B$ obtained from the B pixels. Therefore, the resolution of the second image obtained when the light source unit 3 emits the second illumination light (narrow band light) becomes higher than the resolution of the second image obtained when the light source unit 3 emits the first illumination light (white light).

In contrast, when the light source unit 3 emits the first illumination light, the Cy pixels can acquire a large amount of information on the green wavelength band $H_G$, which is obtainable from the Cy pixels. Assuming that the G pixels are included as in a color filter 202*d* illustrated in FIG. 20, when the light source unit 3 emits the first illumination light, the first image generated by the image processing unit 41 is a sum of information on the green wavelength band $H_G$ obtained from the Cy pixels and information on the green wavelength band $H_G$ obtained from the G pixels. Therefore, the resolution of the first image obtained when the light source unit 3 emits the first illumination light becomes higher than the resolution of the first image obtained when the light source unit 3 emits the second illumination light to the color filter 202*d*. However, when the G pixels are not included as in the color filter 202 illustrated in FIG. 4, only the Cy pixels acquire information on the green wavelength band $H_G$; therefore, the resolution remains the same both when the first illumination light is emitted and when the second illumination light is emitted.

In this manner, the resolution of the first image obtained when the light source unit 3 emits the first illumination light (white light) becomes equal to or higher than the resolution of the first image obtained when the light source unit 3 emits the second illumination light (narrow band light). Further, the resolution of the second image obtained when the light source unit 3 emits the second illumination light (narrow band light) becomes higher than the resolution of the second image obtained when the light source unit 3 emits the first illumination light (white light). Furthermore, the resolution of the first image becomes higher than the resolution of the second image when the light source unit 3 emits the first illumination light (white light), and the resolution of the first image becomes lower than the resolution of the second image when the light source unit 3 emits the second illumination light (narrow band light).

Process Performed by Endoscope Device

Figure 11:
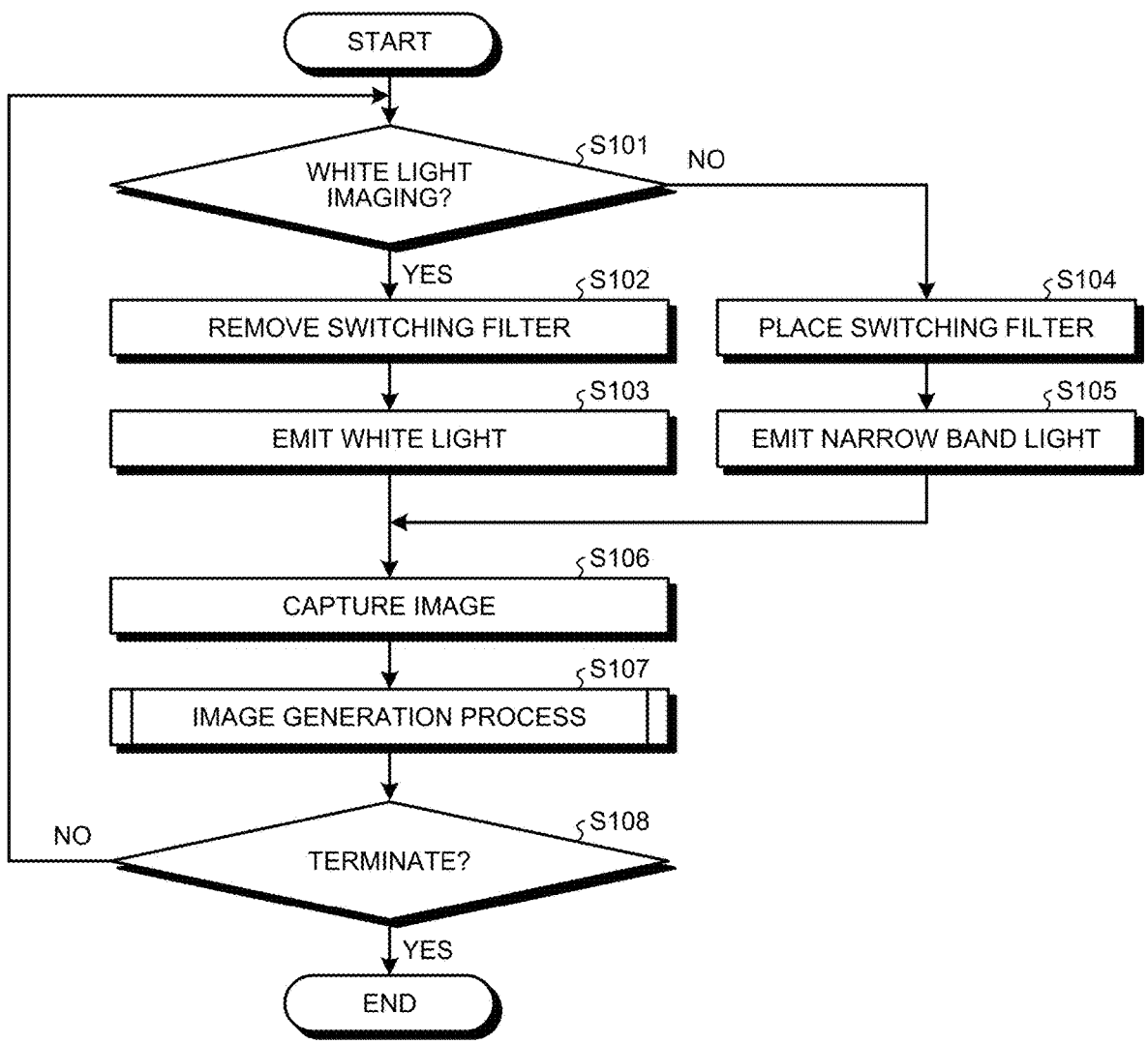
FIG. 11 is a flowchart illustrating an outline of a process performed by the endoscope device according to the first embodiment of the present disclosure.

Next, a process performed by the endoscope device 1 will be described. FIG. 11 is a flowchart illustrating an outline of a process performed by the endoscope device 1. As illustrated in FIG. 11, first, the illumination control unit 32 determines whether or not an observation system is white light imaging on the basis of information from the processor 4 (Step S101). If the observation system is the white light imaging (Step S101: Yes), the illumination control unit 32 drives the driving unit 31*d* to cause the switching filter 31*c* to be removed from the optical path of the white light emitted by the light source 31*a* (Step S102), and causes the light source unit 3 to emit the white light (Step S103). After Step S103, the process by the endoscope device 1 proceeds to Step S106 to be described later.

At Step S101, if the observation system is not the white light imaging (Step S101: No), the illumination control unit 32 drives the driving unit 31*d* to cause the switching filter 31*c* to be placed into the optical path of the white light emitted by the light source 31*a* (Step S104), and causes the light source unit 3 to emit the narrow band light (Step S105). After Step S105, the process by the endoscope device 1 proceeds to Step S106 as described below.

At Step S106, the endoscope 2 captures an image of a subject. In this case, the endoscope 2 outputs an electrical signal generated by the imaging device 201 to the processor 4.

Subsequently, the processor 4 performs image processing on the electrical signal input from the endoscope 2, and performs an image generation process of generating an image to be displayed by the display unit 5 (Step S107). Details of the image generation process will be described later.

Thereafter, if an instruction signal for terminating observation of the subject is input from the input unit 42 (Step S108: Yes), the endoscope device 1 terminates the process. In contrast, if the instruction signal for terminating observation of the subject is not input from the input unit 42 (Step S108: No), the process by the endoscope device 1 returns to Step S101 described above.

Image Generation Process

Figure 12:
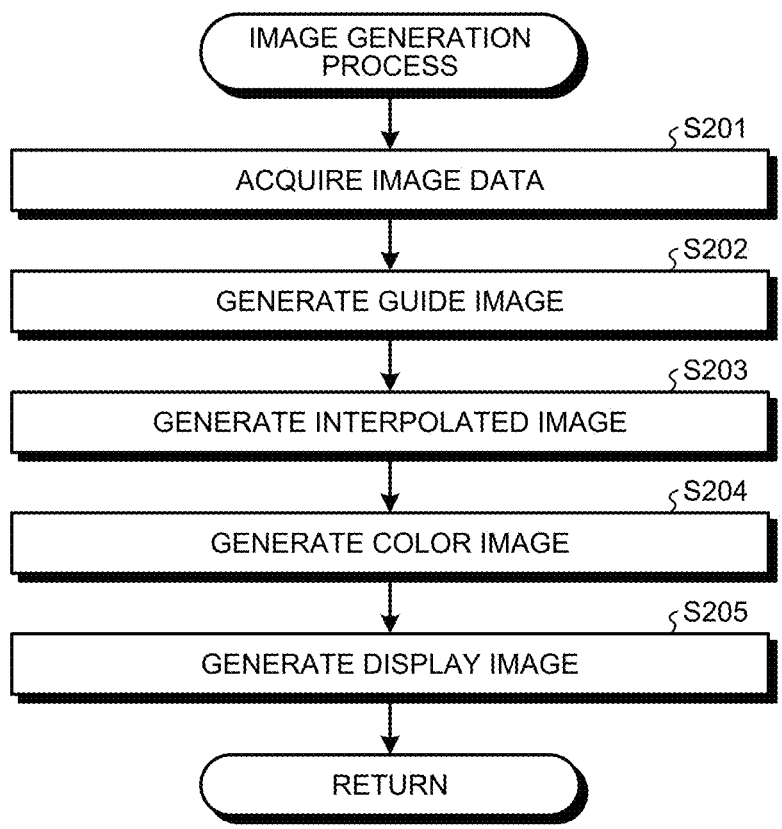
FIG. 12 is a flowchart illustrating an outline of an image generation process according to the first embodiment of the present disclosure.
Figure 13:
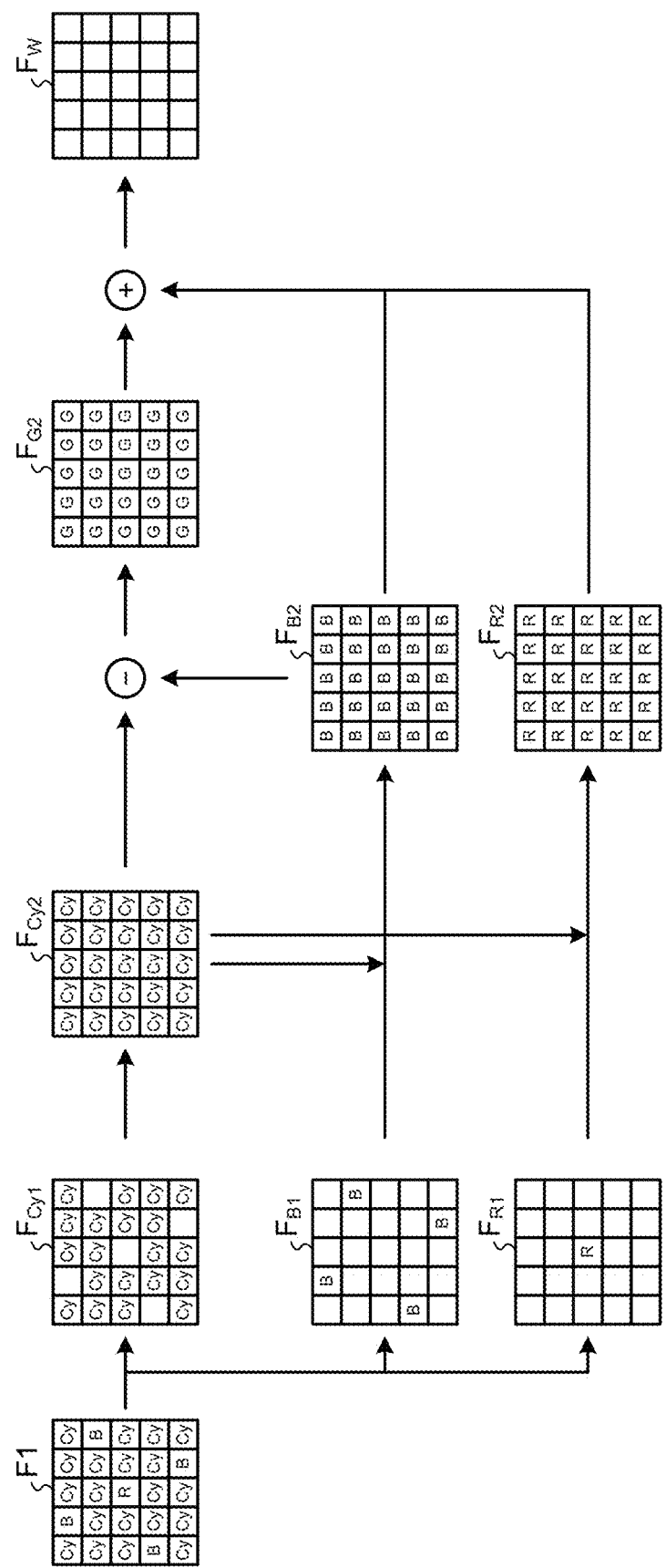
FIG. 13 is a schematic diagram for explaining the outline of the image generation process performed by an image processing unit according to the first embodiment of the present disclosure.

Next, details of the image generation process explained at Step S107 in FIG. 11 will be described. FIG. 12 is a flowchart illustrating an outline of the image generation process. FIG. 13 is a schematic diagram for explaining the outline of the image generation process performed by the image processing unit 41.

As illustrated in FIG. 12, first, the image processing unit 41 acquires image data from the endoscope 2 (Step S201). Specifically, as illustrated in FIG. 13, the image processing unit 41 acquires an image F1 corresponding to the image data from the endoscope 2.

Subsequently, the guide image generating unit 411 generates, as a guide image, an interpolated image of the Cy pixels that are most densely arranged in the imaging device 201 (Step S202). Specifically, as illustrated in FIG. 13, the guide image generating unit 411 performs an interpolation process to calculate a luminance value of a Cy pixel at a pixel position at which each of the B pixels and the R pixel is arranged in the imaging device 201, on the basis of a luminance value (pixel value) of each of the Cy pixels in a separated image $F_{Cy1}$ that is obtained by separating luminance values of the Cy pixels from the image F1, and generates an interpolated image $F_{Cy2}$, in which the luminance values of the Cy pixels are provided at all of the pixel positions, as a guide image (hereinafter, referred to as a "guide image $F_{Cy2}$"). As illustrated in FIG. 13, the pixel position at which each of the B pixels and the R pixel is arranged in the separated image $F_{Cy1}$ is surrounded by the Cy pixels in all of eight adjacent directions (horizontal directions, vertical directions, and oblique directions). Therefore, the guide image generating unit 411 generates the guide image $F_{Cy2}$ using well-known bilinear interpolation, cubic interpolation, direction determination interpolation, or the like. With this operation, the guide image generating unit 411 can generate the guide image $F_{Cy2}$ with high accuracy.

Subsequently, the interpolated image generating unit 412 generates interpolated images of the other colors, that is, the R pixel and the B pixels in the first embodiment, on the basis of the guide image $F_{Cy2}$ that is generated by the guide image generating unit 411 at Step S202 described above (Step S203). Specifically, as illustrated in FIG. 13, the interpolated image generating unit 412 performs an interpolation process to calculate a luminance value of a B pixel at a pixel position at which each of the Cy pixels and the R pixel is arranged in a separated image $F_{B1}$, on the basis of the guide image $F_{Cy2}$ generated by the guide image generating unit 411, and generates an interpolated image $F_{B2}$ (second image) in which the luminance values of the B pixels are provided at all of the pixel positions. Further, as illustrated in FIG. 13, the interpolated image generating unit 412 performs an interpolation process to calculate a luminance value of an R pixel at a pixel position at which each of the Cy pixels and the B pixels is arranged in a separated image $F_{R1}$, on the basis of the guide image $F_{Cy2}$ generated by the guide image generating unit 411, and generates an interpolated image $F_{R2}$ in which the luminance values of the R pixels are provided at all of the pixel positions. Here, the interpolated image generating unit 412 may use a well-known joint bilateral interpolation process, a guided filter interpolation process, or the like as an interpolation method based on the guide image $F_{Cy2}$. With this operation, the interpolated image generating unit 412 can generate the interpolated image $F_{B2}$ and the interpolated image $F_{R2}$ with high accuracy with respect to the B pixels and the R pixel that are less densely arranged in the imaging device 201.

Further, in the first embodiment, the guide image $F_{Cy2}$ is constituted of the Cy pixels that include B components; therefore, a correlation between the Cy pixel and the B pixel is extremely high. Therefore, the interpolated image generating unit 412 can perform an interpolation process based on the guide image $F_{Cy2}$ with high accuracy. Furthermore, a correlation between the R pixel, the G pixel, and the B pixel of a high-frequency component in the white light is generally high. Therefore, even when interpolating the R pixel using a Cy image as the guide image $F_{Cy2}$, the interpolated image generating unit 412 can perform the interpolation process with high accuracy. In a case of the narrow band imaging, the interpolated image generating unit 412 generates a color image using a B image and a G image, and therefore need not generate an R interpolated image. Further, in the case of the narrow band imaging, the Cy pixels have sensitivity to light of the green wavelength band $H_G$ and light of the blue wavelength band $H_B$; therefore, the image processing unit 41 can generate, as the second image, the interpolated image $F_{B2}$ (the image obtained by adding the guide image $F_{Cy2}$ and the separated image $F_{B1}$ in FIG. 13) that has higher resolution than the image obtained by the white light imaging, on the basis of the imaging signal generated by the imaging device 201. Furthermore, in the case of the narrow band imaging, the image processing unit 41 can generate, as the second image, the interpolated image $F_{B2}$ that has higher resolution than an interpolated image $F_{G2}$ that serves as the first image.

Thereafter, the color image generating unit 413 generates the interpolated image $F_{G2}$ (first image), in which luminance values of G pixels are provided as all of the pixel values, using the guide image $F_{Cy2}$ generated by the guide image generating unit 411 at Step S202 described above and the interpolated image $F_{B2}$ generated by the interpolated image generating unit 412 at Step S203 described above. Specifically, the color image generating unit 413 separates G components from the guide image $F_{Cy2}$ by performing a subtraction process of subtracting the luminance value of each of the pixels of the interpolated image $F_{B2}$ constituted of the B pixels from the guide image $F_{Cy2}$ constituted of the Cy pixels, and generates the interpolated image $F_{G2}$ of the G pixels. More specifically, the color image generating unit 413 generates the interpolated image $F_{G2}$ of the G pixels by Equation (1) below.

$$G(i,j)=Cy(i,j)-\alpha \times B(i,j) \quad (1)$$

Here, G(i, j) represents a luminance value (pixel value) of each of the G pixels of the interpolated image $F_{G2}$, Cy(i, j) represents a luminance value (pixel value) of each of the Cy pixels of the interpolated image $F_{Cy2}$, B(i, j) represents a luminance value (pixel value) of each of the B pixels of the interpolated image $F_{B2}$, and α represents a G correction coefficient as a parameter that is calculated in advance from a ratio between the blue wavelength band $H_B$ and the green wavelength band $H_G$ in the spectral characteristic of the light source 31a and the Cy pixel.

Subsequently, when the endoscope device 1 performs the white light imaging, the color image generating unit 413 generates a color image $F_W$ using the interpolated image $F_{G2}$, the interpolated image $F_{B2}$, and the interpolated image $F_{R2}$. Specifically, the color image generating unit 413 generates the color image $F_W$ by adding the interpolated image $F_{G2}$, the interpolated image $F_{B2}$, and the interpolated image $F_{R2}$ illustrated in FIG. 13. In contrast, when the endoscope device 1 performs the narrow band imaging, the color image generating unit 413 generates a color image using the interpolated image $F_{G2}$ and the interpolated image $F_{B2}$ (Step S204).

Thereafter, the display image generating unit 414 generates a display image using the color image Fw generated by the color image generating unit 413 (Step S205). Specifically, the display image generating unit 414 performs a tone modulation process, an enlargement process, a demosaicing process, a structure enhancement process for structures, such as capillaries or fine mucosal patterns on a mucosal surface, or the like on the color image $F_W$, and generates a display image to be displayed. In this case, the display image generating unit 414 may perform the structure enhancement process using information on the guide image $F_{Cy2}$ generated at Step S202, such as edge information or luminance information, for example. The interpolated image $F_{Cy2}$ has high resolution regardless of the observation system; therefore, it is possible to perform each process, such as the structure enhancement process, with high accuracy. After Step S205, the process by the endoscope device 1 returns to the main routine in FIG. 11.

According to the first embodiment of the present disclosure as described above, the color filter 202 includes the Cy filters, the B filters, and the R filters such that the number of the Cy filters is equal to or larger than the number of the B filters that are a certain type of filters that are most frequently arranged in the color filter 202. Therefore, it is possible to obtain an image with high accuracy in both observation methods of the white light imaging and the narrow band imaging.

Further, according to the first embodiment of the present disclosure, when the light source unit 3 emits white light as the first illumination light, light of the green wavelength band $H_G$ is emitted with higher intensity than light of the blue wavelength band $H_B$, and, when the light source unit 3 emits narrow band light as the second illumination light, light of the blue wavelength band $H_B$, is emitted with higher intensity than light of the green wavelength band $H_G$. Therefore, it is possible to obtain an image with high accuracy in both observation methods of the white light imaging and the narrow band imaging.

Furthermore, according to the first embodiment of the present disclosure, the interpolated image generating unit 412 performs an interpolation process to calculate a luminance value of a B pixel at a pixel position at which each of the Cy pixels and the R pixel is arranged in the separated image $F_{B1}$, on the basis of the guide image $F_{Cy2}$ generated by the guide image generating unit 411, and generates the interpolated image $F_{B2}$ in which the luminance values of the B pixels are provided at all of the pixel positions. Moreover, the interpolated image generating unit 412 performs an interpolation process to calculate a luminance value of an R pixel at a pixel position at which each of the Cy pixels and the B pixels is arranged in the separated image $F_{R1}$, and generates the interpolated image $F_{R2}$ in which the luminance values of the R pixels are provided at all of the pixel positions. Therefore, it is possible to perform an interpolation process with high accuracy.

Furthermore, according to the first embodiment, the white light emitted by the light source unit 3 has higher intensity in the green wavelength band $H_G$ than in the blue wavelength band $H_B$, and the narrow band light emitted by the light source unit 3 has higher intensity in the blue wavelength band $H_B$ than in the green wavelength band $H_G$; however, the intensity of the wavelength band emitted by the light source unit 3 is not limited to this example. Any light including the blue wavelength band $H_B$ and the green wavelength band $H_G$ may be employed. The Cy pixel can acquire information on the blue wavelength band $H_B$ and information on the green wavelength band $H_G$ regardless of a characteristic of the light source. Therefore, when the light source unit 3 emits the second illumination light, the second image is obtained as a sum of the information on the blue wavelength band $H_B$ acquired from the Cy pixels and the information on the blue wavelength band $H_B$ acquired from the B pixels, and, when the light source unit 3 emits the first illumination light, the first image is obtained as a sum of the information on the green wavelength band $H_G$ acquired from the Cy pixels and the information on the green wavelength band $H_G$ acquired from the G pixels. That is, it is possible to obtain an image with high resolution in both observation methods of the white light imaging and the narrow band imaging.

First Modification of First Embodiment

Figure 14:
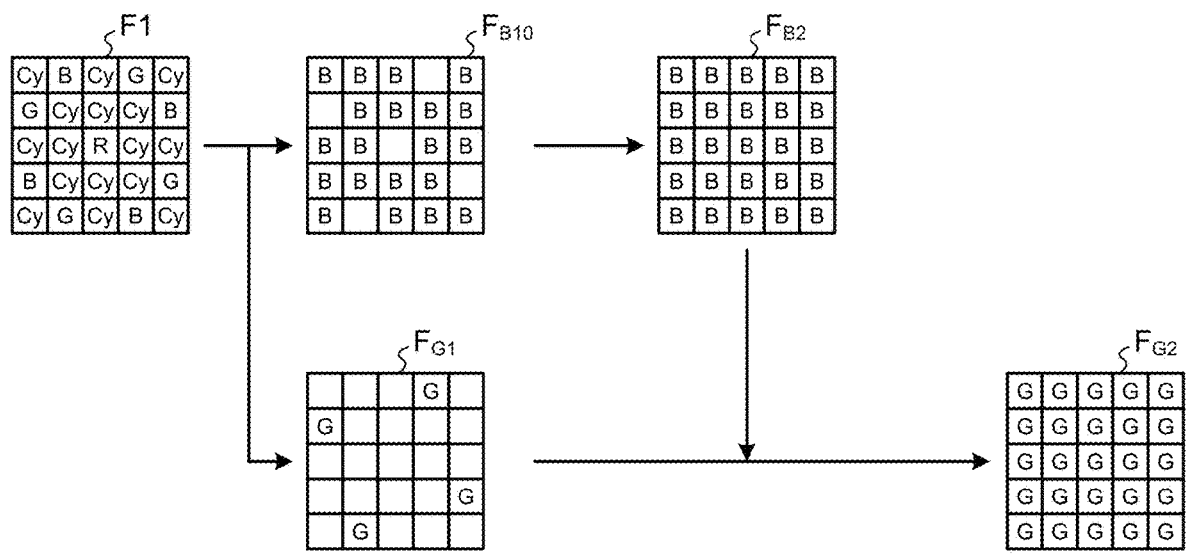
FIG. 14 is a diagram illustrating an example of a color image that is generated through narrow band imaging by an image processing unit according to a first modification of the first embodiment of the present disclosure.

Next, a first modification of one embodiment of the present disclosure will be described. FIG. 14 is a diagram illustrating an example of a color image that is generated through narrow band imaging by an image processing unit according to a first modification of the first embodiment of the present disclosure.

As illustrated in FIG. 14, when the endoscope device 1 performs the narrow band imaging, the interpolated image generating unit 412 may generate the interpolated image $F_{B2}$ by assuming that Cy pixels serve as B pixels as in an image $F_{B10}$ because the Cy pixels can acquire information that is highly similar to information acquired by the G pixels or the B pixels. Then, the color image generating unit 413 may generate a color image of narrow band light using the interpolated image $F_{B2}$ and the interpolated image $F_{G2}$ generated by the interpolated image generating unit 412. Further, when the endoscope device 1 performs the white light imaging, the interpolated image generating unit 412 may generate the interpolated image $F_{G2}$ by assuming that Cy pixels serve as G pixels, similarly to the case of the narrow band imaging. That is, the interpolated image generating unit 412 may generate the interpolated image $F_{G2}$ using the interpolated image $F_{B2}$ and a separated image $F_{G1}$.

According to the first modification of the first embodiment of the present disclosure as described above, it is possible to simplify the image processing performed by the image processing unit 41 as compared to the first embodiment described above.

Second Modification of First Embodiment

Figure 15:
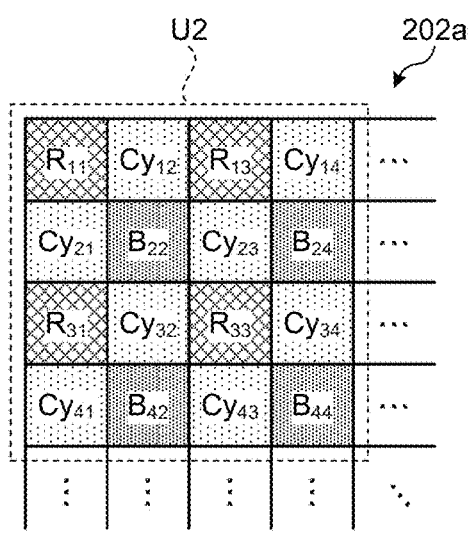
FIG. 15 is a schematic diagram illustrating an example of a configuration of a color filter according to a second modification of the first embodiment of the present disclosure.

Next, a second modification of the first embodiment of the present disclosure will be described. FIG. 15 is a schematic diagram illustrating an example of a configuration of a color filter according to the second modification of the first embodiment of the present disclosure.

A color filter 202a illustrated in FIG. 15 is configured such that filter units U2, each of which includes 16 filters arranged in a two-dimensional 4×4 matrix, are arranged in accordance with arrangement of the pixels $P_{ij}$. The filter unit U2 is configured such that the Cy filters are arranged instead of the G filters at positions where the G filters are arranged in the conventional Bayer arrangement. Specifically, the filter unit U2 includes four R filters, four B filters, and eight Cy filters. Further, in the filter unit U2, the number of the Cy filters is equal to or larger than the number of the B filters or the R filters that are most frequently arranged in the color filter 202a. That is, the filter unit U2 is configured such that the Cy filters are arranged in a checkered-flag pattern. Further, a ratio between the number of the Cy filters and the number of the B filters is 2:1.

According to the second modification of the first embodiment of the present disclosure, it is possible to obtain an image with high accuracy in both observation methods of the white light imaging and the narrow band imaging, similarly to the first embodiment described above.

Second Embodiment

Next, a second embodiment of the present disclosure will be described. In the first embodiment described above, one type of a complementary color filter is arranged in the filter unit, but in the second embodiment, another type of a complementary color filter is arranged in the filter unit. In the following, a configuration of a color filter according to the second embodiment is first described, and then image processing performed by an image processing unit according to the second embodiment will be described. The same components as those of the endoscope device 1 according to the first embodiment described above are denoted by the same reference signs, and explanation thereof will be omitted.

Configuration of Color Filter

Figures 16, 17:
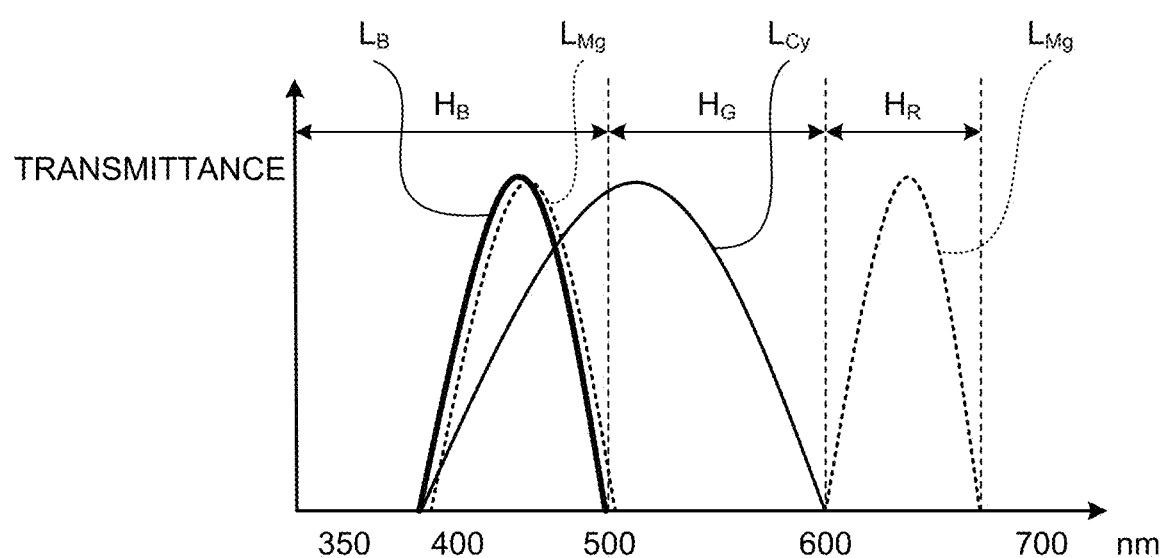
FIG. 16 is a schematic diagram illustrating an example of a configuration of a color filter according to a second embodiment of the present disclosure.
FIG. 17 is a diagram illustrating an example of a transmission characteristic of each of filters included in a color filter according to the second embodiment of the present disclosure.

FIG. 16 is a schematic diagram illustrating an example of the configuration of the color filter according to the second embodiment of the present disclosure. As illustrated in FIG. 16, a color filter 202b is configured using filter units U3, in each of which a magenta filter (hereinafter, referred to as an "Mg filter") is arranged instead of the R filter described above. When the Mg filter is arranged at a position corresponding to the pixel $P_{ij}$, the Mg filter is denoted by $Mg_{ij}$. In the second embodiment, the Mg filter functions as a third filter.

Transmission Characteristic of Each Filter

Next, a transmission characteristic of each of the filters included in the color filter 202b will be described. FIG. 17 is a diagram illustrating an example of the transmission characteristic of each of the filters included in the color filter 202b. In FIG. 17, a horizontal axis represents a wavelength and a vertical axis represents a transmittance. Further, in FIG. 17, a curved line $L_B$ represents a transmittance curve of the B filter, a curved line $L_{Cy}$ represents a transmittance curve of the Cy filter, and a curved line $L_{Mg}$ represents a transmittance curve of the Mg filter.

As illustrated in FIG. 17, the Mg filter transmits light of the red wavelength band $H_R$ and light of the blue wavelength band $H_B$. That is, the Mg filter transmits light of a magenta wavelength band, where the magenta is a complementary color. When the light source unit 3 emits narrow band light, the pixel $Mg_{ij}$ is not able to acquire information on the red wavelength band $H_R$, and therefore is assumed as a pixel that acquires the same information as the B pixel. Therefore, when the endoscope device 1 performs the narrow band imaging, information on the B pixels is increased, so that it becomes possible to obtain an image with increased resolution.

Image Generation Process

Figure 18:
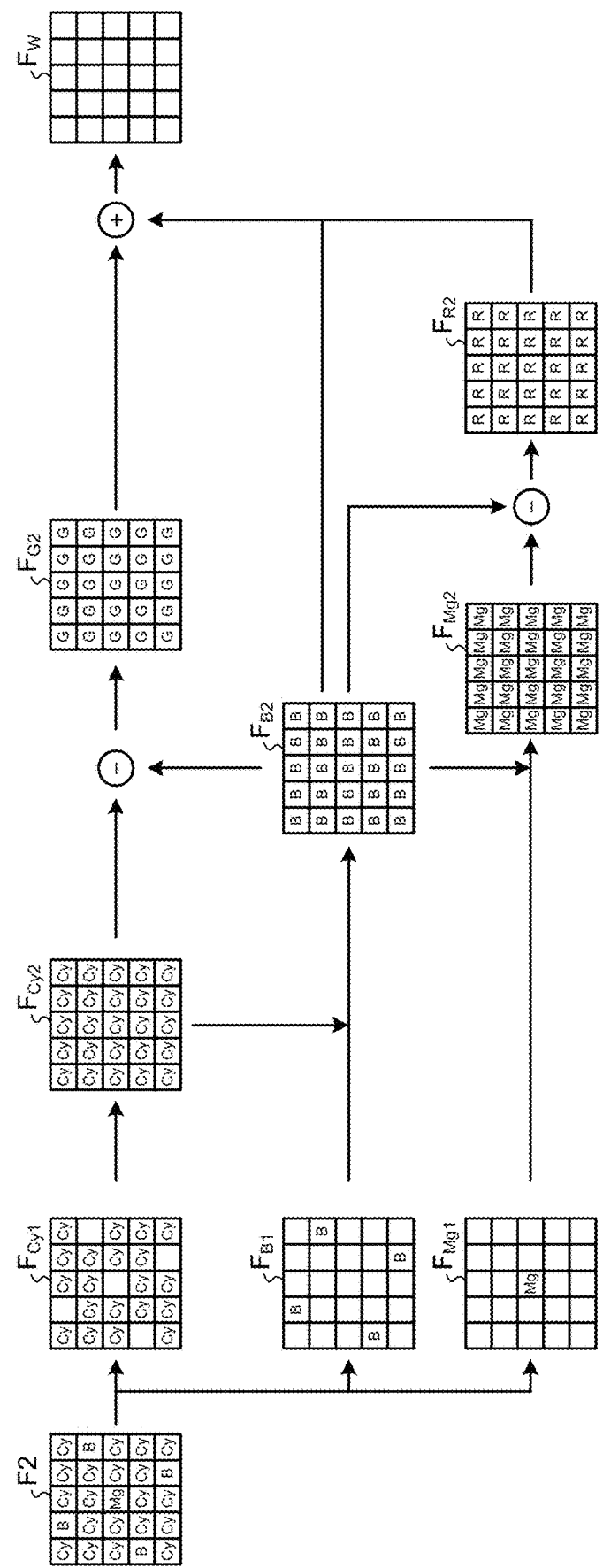
FIG. 18 is a schematic diagram for explaining an outline of an image generation process performed by an image processing unit according to the second embodiment of the present disclosure.

Next, an image generation process performed by the image processing unit 41 will be described. FIG. 18 is a schematic diagram for explaining an outline of the image generation process performed by the image processing unit 41.

As illustrated in FIG. 18, similarly to the first embodiment described above, the guide image generating unit 411 performs an interpolation process to calculate a luminance value of a Cy pixel at a pixel position at which each of the B pixels and the Mg pixels is arranged in the imaging device 201, on the basis of the luminance value (pixel value) of each of the Cy pixels in the separated image $F_{Cy1}$ that is obtained by separating the luminance values of the Cy pixels from an image F2, and generates the guide image $F_{Cy2}$ in which the luminance values of the Cy pixels are provided at all of the pixel positions.

Thereafter, the interpolated image generating unit 412 performs an interpolation process to calculate a luminance value of a B pixel at a pixel position at which each of the Cy pixels and the Mg pixel is arranged in the separated image $F_{B1}$, on the basis of the guide image $F_{Cy2}$ generated by the guide image generating unit 411, and generates the interpolated image $F_{B2}$ (second image) in which the luminance values of the B pixels are provided at all of the pixel positions. With this operation, in the case of the narrow band imaging, the image processing unit 41 can generate, as the second image, the interpolated image $F_{B2}$ that has higher resolution than the image obtained by the white light imaging, on the basis of the imaging signal generated by the imaging device 201. Furthermore, in the case of the narrow band imaging, the image processing unit 41 can generate, as the second image, the interpolated image $F_{B2}$ that has higher resolution than the interpolated image $F_{G2}$ that serves as the first image.

Subsequently, the interpolated image generating unit 412 performs an interpolation process to calculate a luminance value of an Mg pixel at a pixel position at which each of the Cy pixels and the B pixels is arranged in a separated image $F_{Mg1}$, on the basis of the interpolated image $F_{B2}$, and generates an interpolated image $F_{Mg2}$ in which the luminance values of the Mg pixels are provided at all of the pixel positions.

Then, the color image generating unit 413 separates R components from the interpolated image $F_{Mg2}$ by performing a subtraction process of subtracting the luminance value of each of the pixels of the interpolated image $F_{B2}$ constituted of the B pixels from the interpolated image $F_{Mg2}$ constituted of the Mg pixels generated by the interpolated image generating unit 412, and generates the interpolated image $F_{R2}$ of the R pixel. With this operation, the color image generating unit 413 generates the interpolated image $F_{R2}$ from the interpolated image $F_{Mg2}$ that is generated using the interpolated image $F_{B2}$ by the interpolated image generating unit 412, and performs an interpolation process using information on the color on which the subtraction process is performed in a color image generation process. Therefore, it is possible to prevent an increase in noise during the subtraction process.

According to the second embodiment of the present disclosure as described above, it is possible to obtain an image with high accuracy in both observation methods of the white light imaging and the narrow band imaging, similarly to the first embodiment described above.

Further, according to the second embodiment of the present disclosure, the Mg filter is arranged in the filter unit U3 and an interpolation process is performed using information on the color on which the subtraction process is performed during the color image generation process. Therefore, it is possible to prevent an increase in noise during the subtraction process.

First Modification of Second Embodiment

Figure 19:
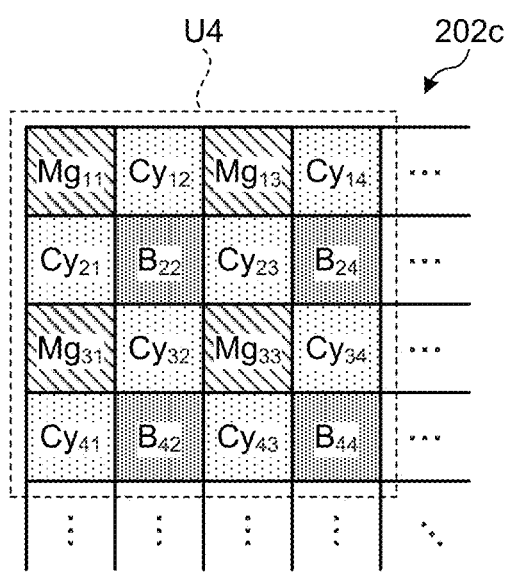
FIG. 19 is a schematic diagram illustrating an example of a configuration of a color filter according to a first modification of the second embodiment of the present disclosure.

Next, a first modification of the second embodiment of the present disclosure will be described. FIG. 19 is a schematic diagram illustrating an example of a configuration of a color filter according to the first modification of the second embodiment of the present disclosure.

A color filter 202c illustrated in FIG. 19 is configured such that filter units U4, each of which includes 16 filters arranged in two-dimensional 4×4 matrix, are arranged in accordance with arrangement of the pixels $P_{ij}$. The filter unit U4 is configured such that the Cy filters are arranged instead of the G filters at positions where the G filters are arranged in the conventional Bayer arrangement, and the Mg filters are arranged instead of the R filters at position where the R filters are arranged in the conventional Bayer arrangement. Specifically, the filter unit U4 includes four Mg filters, four B filters, and eight Cy filters. Further, the filter unit U4 is configured such that the number of the Cy filters is equal to or larger than the number of the B filters or the Mg filters that are most frequently arranged in the color filter 202c. Furthermore, the filter unit U4 is configured such that the Cy filters are arranged in a checkered-flag pattern. Moreover, a ratio among the number of the Cy filters, the number of the B filters, and the number of the Mg filters is 2:1:1.

With the color filter 202c configured as described above, it is possible to obtain an image with high accuracy in both observation methods of the white light imaging and the narrow band imaging, similarly to the first embodiment described above.

Third Embodiment

Next, a third embodiment of the present disclosure will be described. In the first embodiment described above, the filter unit is configured using three kinds of filters. However, in the third embodiment, a filter unit is configured using four kinds of filters. In the following, a configuration of a color filter according to the third embodiment will be first described, and then image processing performed by an image processing unit according to the third embodiment will be described. The same components as those of the endoscope device 1 according to the first embodiment described above are denoted by the same reference signs, and explanation thereof will be omitted.

<Configuration of Color Filter>

Figure 20:
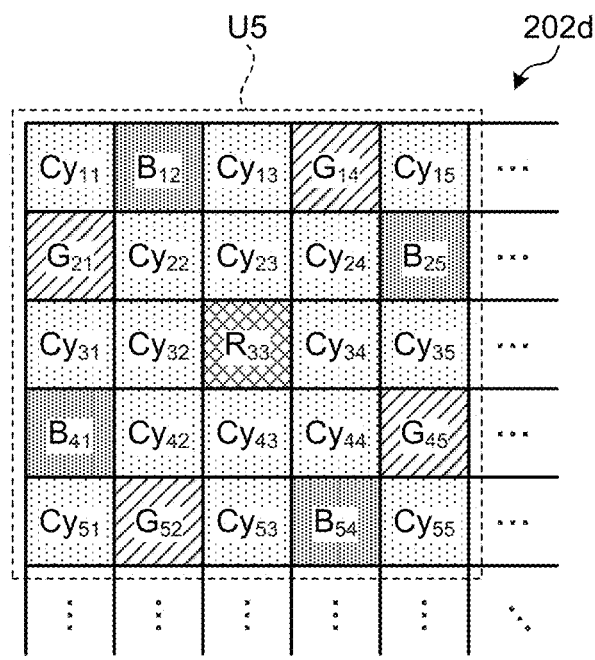
FIG. 20 is a schematic diagram illustrating an example of a configuration of a color filter according to a third embodiment of the present disclosure.

FIG. 20 is a schematic diagram illustrating an example of the color filter according to the third embodiment of the present disclosure.

The color filter 202d illustrated in FIG. 20 is configured such that filter units U5, each of which includes 25 filters arranged in two-dimensional 5×5 matrix, are arranged in accordance with arrangement of the pixels $P_{ij}$. The filter unit U5 includes one R filter, four B filters, four G filters, and 16 Cy filters. Further, the filter unit U5 is configured such that the number of the Cy filters is equal to or larger than the number of the B filters and the G filters that are most frequently arranged in the color filter 202d.

Transmission Characteristic of Each Filter

Figure 21:
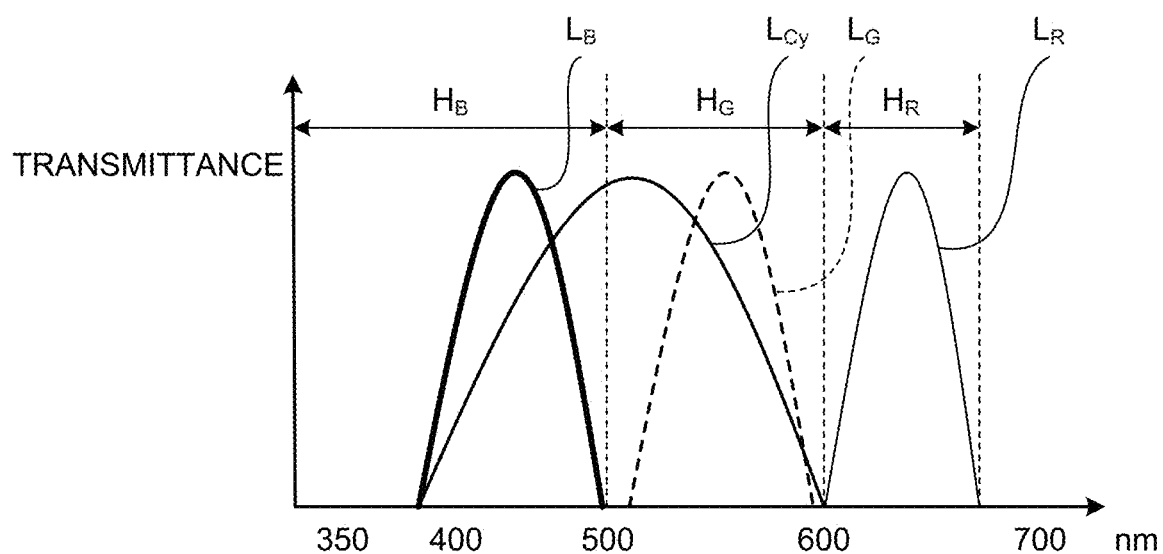
FIG. 21 is a diagram illustrating an example of a transmission characteristic of each of filters included in the color filter according to the third embodiment of the present disclosure.

Next, a transmission characteristic of each of the filters included in the color filter 202d will be described. FIG. 21 is a diagram illustrating an example of the transmission characteristic of each of the filters included in the color filter 202d. In FIG. 21, a curved line $L_B$ represents a transmittance curve of the B filter, a curved line $L_R$ represents a transmittance curve of the R filter, a curved line $L_G$ represents a transmittance curve of the G filter, and a curved line $L_{Cy}$ represents a transmittance curve of the Cy filter. Further, in FIG. 21, a horizontal axis represents a wavelength and a vertical axis represents a transmittance. As illustrated in FIG. 21, the G filter transmits light of the wavelength band $H_G$.

Figure 22:
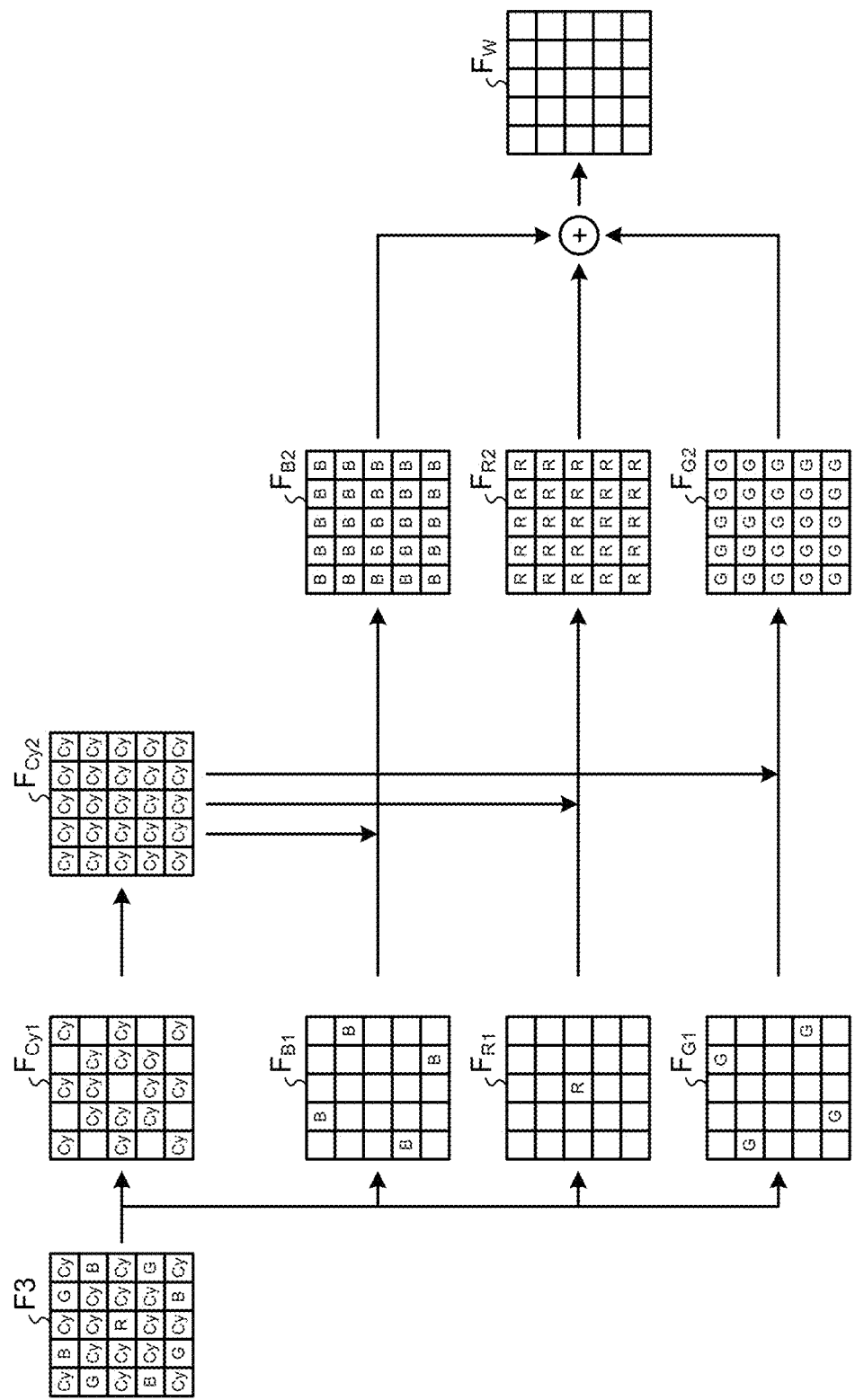
FIG. 22 is a schematic diagram for explaining an outline of an image generation process performed by an image processing unit according to the third embodiment of the present disclosure.

Image Generation Process Next, an image generation process performed by the image processing unit 41 will be described. FIG. 22 is a schematic diagram for explaining an outline of the image generation process performed by the image processing unit 41.

As illustrated in FIG. 22, the interpolated image generating unit 412 generates interpolated images of the other color pixels, that is, the R pixel and the B pixel in the third embodiment, on the basis of the guide image generated by the guide image generating unit 411. Specifically, the guide image generating unit 411 generates the guide image $F_{Cy2}$, on the basis of each of the Cy pixels in the separated image $F_{Cy1}$ obtained by separating luminance values of the Cy pixels from an image F3. The interpolated image generating unit 412 generates each of the interpolated image $F_{B2}$ (second image), the interpolated image $F_{R2}$, and the interpolated image $F_{G2}$ (first image) on the basis of the guide image $F_{Cy2}$ generated by the guide image generating unit 411. With this operation, the color image generating unit 413 can omit a subtraction process of subtracting the luminance value of each of the pixels of the interpolated image $F_{B2}$ constituted of the B pixels from the guide image $F_{Cy2}$. Therefore, when the endoscope device 1 performs the white light imaging, it is possible to ensure high color reproducibility. Further, in the case of the narrow band imaging, the image processing unit 41 can generate, as the second image, the interpolated image $F_{B2}$ that has higher resolution than the image obtained by the white light imaging, on the basis of the imaging signal generated by the imaging device 201. Furthermore, in the case of the narrow band imaging, it is possible to generate, as the second image, the interpolated image $F_{B2}$ that has higher resolution than the interpolated image $F_{G2}$ that serves as the first image.

According to the third embodiment of the present disclosure as described above, it is possible to obtain an image with high accuracy in both observation methods of the white light imaging and the narrow band imaging, similarly to the first embodiment as described above.

Further, according to the third embodiment of the present disclosure, the color image generating unit 413 can omit the subtraction process of subtracting the luminance value of each of the pixels of the interpolated image $F_{B2}$ constituted of the B pixels from the guide image $F_{Cy2}$. Therefore, it is possible to ensure high color reproducibility when the endoscope device 1 performs the white light imaging.

Fourth Embodiment

Next, a fourth embodiment of the present disclosure will be described. In the first embodiment described above, the Cy filters are arranged as the complementary color filters, but in the fourth embodiment, yellow filters (Ye filters) are arranged as complementary color filters. In the following, a configuration of a color filter according to the fourth embodiment is first described, and then an image generation process performed by an image processing unit will be described. The same components as those of the endoscope device 1 according to the first embodiment described above are denoted by the same reference signs, and explanation thereof will be omitted.

Configuration of Color Filter

Figures 23, 24:
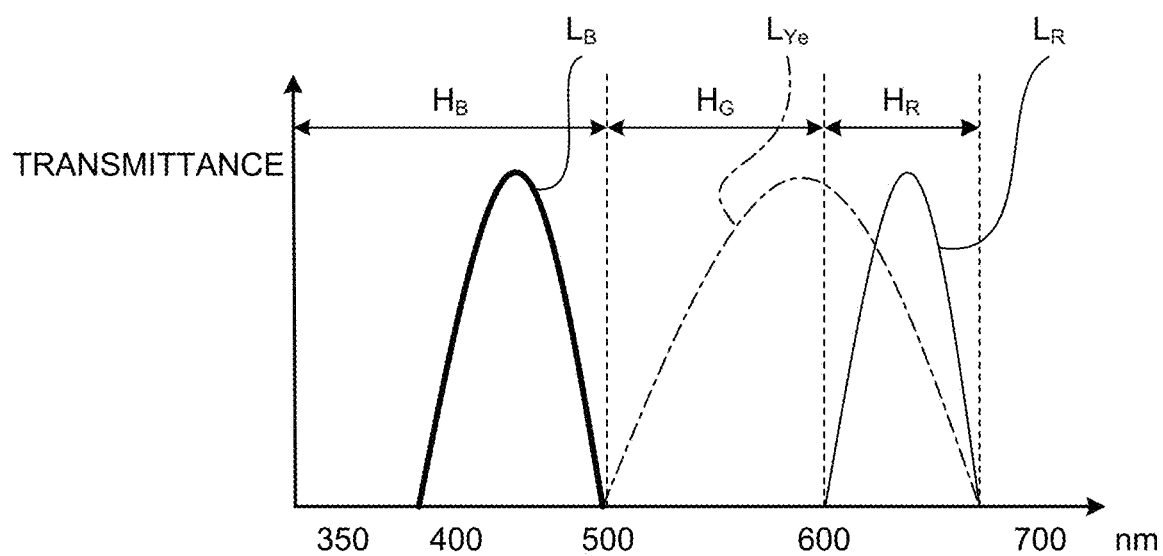
FIG. 23 is a schematic diagram illustrating an example of a configuration of a color filter according to a fourth embodiment of the present disclosure.
FIG. 24 is a diagram illustrating an example of a transmission characteristic of each of filters included in the color filter according to the fourth embodiment of the present disclosure.

FIG. 23 is a schematic diagram illustrating an example of the configuration of the color filter according to the fourth embodiment of the present disclosure.

A color filter 202e illustrated in FIG. 23 is configured such that filter units U6, each of which includes 25 filters arranged in two-dimensional 5×5 matrix, are arranged in accordance with arrangement of the pixels $P_{ij}$. The filter unit U6 includes four R filters, one B filter, and 20 Ye filters. Further, the filter unit U6 is configured such that the number of the Ye filters is equal to or larger than the number of the R filters that are most frequently arranged in the color filter 202e.

Transmission Characteristic of Each Filter

Next, a transmission characteristics of each of the filters included in the color filter 202e will be described. FIG. 24 is a diagram illustrating an example of the transmission characteristic of each of the filters included in the color filter 202e. In FIG. 24, a curved line $L_B$ represents a transmittance curve of the B filter, a curved line $L_R$ represents a transmittance curve of the R filter, and a curved line $L_{Ye}$ represents a transmittance curve of the Ye filter. Further, in FIG. 24, a horizontal axis represents a wavelength and a vertical axis represents a transmittance.

As illustrated in FIG. 24, the Ye filter transmits light of the red wavelength band $H_R$ and light of the green wavelength band $H_G$. That is, the Ye filter transmits light of a yellow wavelength band, where the yellow is a complementary color.

Spectral Characteristic of Light Emitted by Light Source Unit

Figure 25:
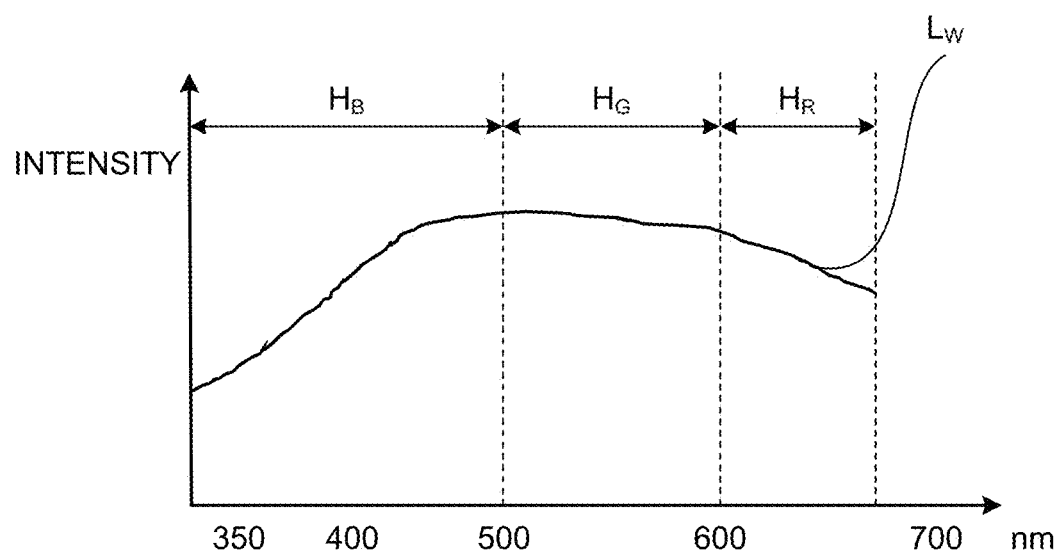
FIG. 25 is a diagram illustrating an example of a spectral characteristic of white light emitted by a light source unit according to the fourth embodiment of the present disclosure.
Figure 26:
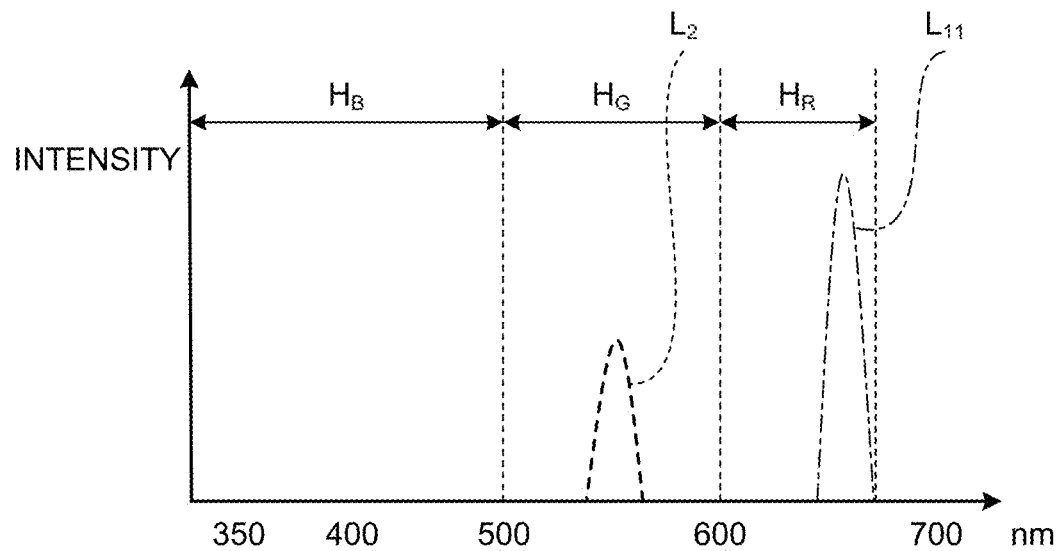
FIG. 26 is a diagram illustrating an example of a spectral characteristic of narrow band light emitted by the light source unit according to the fourth embodiment of the present disclosure.

Next, a spectral characteristic of light emitted by the light source unit 3 will be described. FIG. 25 is a diagram illustrating an example of a spectral characteristic of white light emitted by the light source unit 3. FIG. 26 is a diagram illustrating an example of a spectral characteristic of narrow band light emitted by the light source unit 3. In FIG. 25 and FIG. 26, horizontal axes represent a wavelength and vertical axes represent intensity. In FIG. 25, a curved line $L_W$ represents the spectral characteristic of the white light emitted by the light source unit 3. Further, in FIG. 26, two curved lines $L_2$ and $L_{11}$ represent the spectral characteristic of the narrow band light emitted by the light source unit 3.

As indicated by the curved line $L_W$ in FIG. 25, the white light emitted by the light source unit 3 has higher intensity in the green wavelength band $H_G$ than in the blue wavelength band $H_B$. In contrast, as indicated by the curved line $L_2$ and the curved line $L_{11}$ in FIG. 26, the narrow band light emitted by the light source unit 3 has higher intensity in the red wavelength band $H_R$ than in the green wavelength band $H_G$.

Image Generation Process

Figure 27:
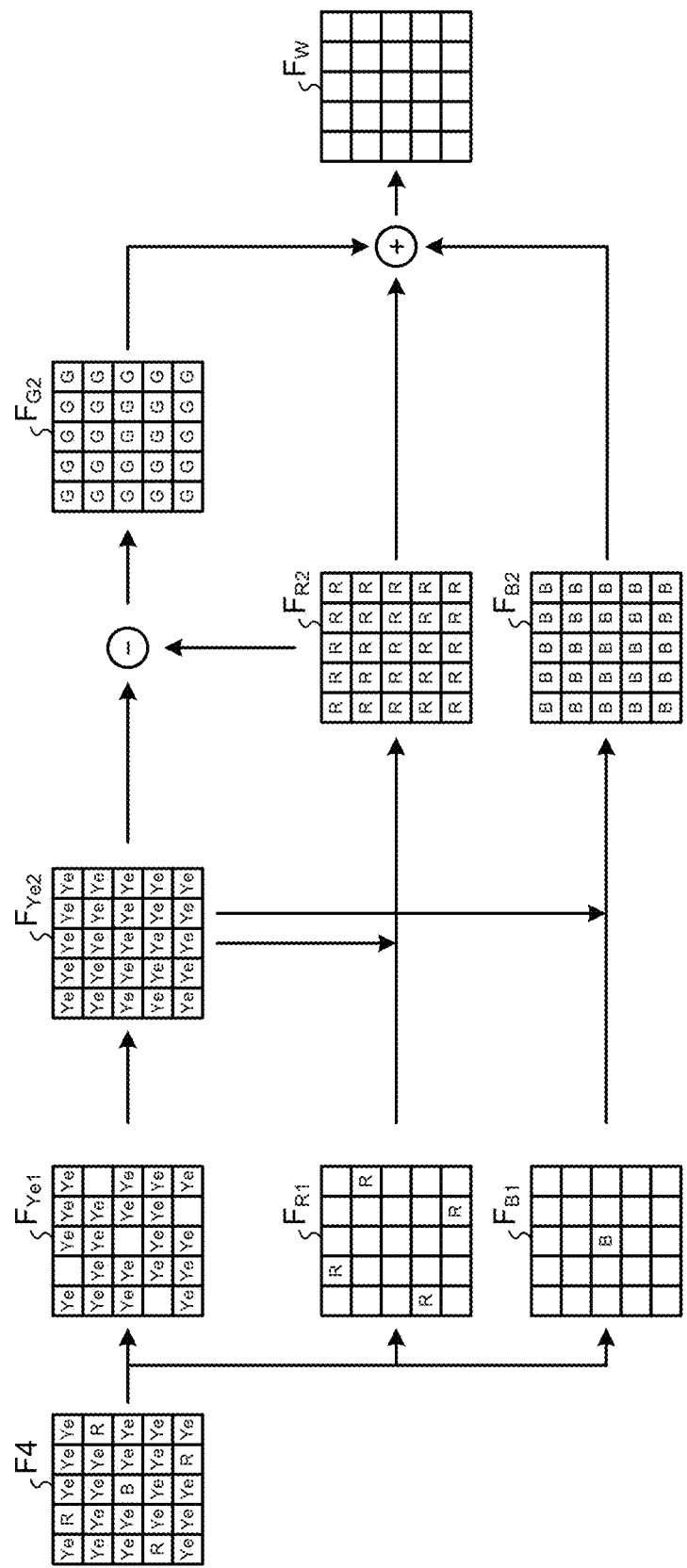
FIG. 27 is a schematic diagram for explaining an outline of an image generation process performed by an image processing unit according to the fourth embodiment of the present disclosure.

Next, an image generation process performed by the image processing unit 41 will be described. FIG. 27 is a schematic diagram for explaining an outline of the image generation process performed by the image processing unit 41.

As illustrated in FIG. 27, first, the guide image generating unit 411 generates, as a guide image, an interpolated image of the Ye pixels. Specifically, as illustrated in FIG. 27, the guide image generating unit 411 performs an interpolation process to calculate a luminance value of a Ye pixel at a pixel position at which each of the B pixels and the R pixels is arranged, on the basis of a luminance value of each of the Ye pixels in a separated image $F_{Ye1}$ that is obtained by separating luminance values of the Ye pixels from an image F4, and generates a guide image $F_{Ye2}$ in which the luminance values of the Ye pixels are provided at all of the pixel positions. As illustrated in FIG. 27, the pixel position at which each of the B pixels and the R pixels are arranged in the separated image $F_{Ye1}$ is surrounded by the Ye pixels in all of eight adjacent directions (horizontal directions, vertical directions, and oblique directions). Therefore, the guide image generating unit 411 generates the guide image $F_{Ye2}$ using well-known bilinear interpolation, cubic interpolation, direction determination interpolation, or the like. With this operation, the guide image generating unit 411 can generate the guide image $F_{Ye2}$ with high accuracy.

Subsequently, the interpolated image generating unit 412 performs an interpolation process to calculate a luminance value of an R pixel at a pixel position at which each of the Ye pixels and the B pixels is arranged in the separated image $F_{R1}$, on the basis of the guide image $F_{Ye2}$ generated by the guide image generating unit 411, and generates the interpolated image $F_{R2}$ (second image) in which the luminance values of the R pixels are provided at all of the pixel positions. Further, the interpolated image generating unit 412 performs an interpolation process to calculate a luminance value of a B pixel at a pixel position at which each of the Ye pixels and the R pixels is arranged in the separated image $F_{B1}$, on the basis of the guide image $F_{Ye2}$ generated by the guide image generating unit 411, and generates the interpolated image $F_{R2}$ in which the luminance values of the B pixels are provided at all of the pixel positions. Here, the interpolated image generating unit 412 may use a well-known joint bilateral interpolation process, a guided filter interpolation process, or the like as an interpolation method based on the guide image $F_{Ye2}$. With this operation, the interpolated image generating unit 412 can generate the interpolated image $F_{R2}$ and the interpolated image $F_{B2}$ with high accuracy with respect to the R pixels and the B pixels that are less densely arranged in the imaging device 201. Further, in the case of the narrow band imaging, the image processing unit 41 can generate the interpolated image $F_{R2}$ (the image obtained by adding the guide image $F_{Ye2}$ and the separated image $F_{R1}$ in FIG. 27) that has higher resolution than the image obtained by the white light imaging, on the basis of the imaging signal generated by the imaging device 201. Furthermore, in the case of the narrow band imaging, it is possible to generate, as the second image, the interpolated image $F_{R2}$ that has higher resolution than the interpolated image $F_{G2}$ that serve as the first image.

Thereafter, the color image generating unit 413 separates R components from the guide image $F_{Ye2}$ by performing a subtraction process of subtracting the luminance value of each of the pixels of the interpolated image $F_{R2}$ constituted of the R pixels from the guide image $F_{Ye2}$ constituted of the Ye pixels, and generates the interpolated image $F_{G2}$ of the G pixels. Then, when the endoscope device 1 performs the white light imaging, the color image generating unit 413 generates the color image $F_W$ using the interpolated image $F_{G2}$, the interpolated image $F_{B2}$, and the interpolated image $F_{R2}$. In contrast, when the endoscope device 1 performs narrow band imaging, the color image generating unit 413 generates a color image using the interpolated image $F_{G2}$ and the interpolated image $F_{R2}$.

According to the fourth embodiment of the present disclosure as described above, by providing the Ye filters that can transmit light of the red wavelength band $H_R$, which is important in the narrow band imaging, and light of the green wavelength band $H_G$, which is important in the white light imaging, it becomes possible to obtain an image with high resolution both in the white light imaging and the narrow band imaging.

Fifth Embodiment

Next, a fifth embodiment of the present disclosure will be described. In the first embodiment described above, the single light source 31a emits white light, but in the fifth embodiment, three light sources that emit light of different wavelength bands emit white light. Specifically, in the first embodiment described above, a spectral characteristic of illumination light emitted by the light source unit 3 during imaging is not adjusted, but in the fifth embodiment, a spectral characteristic of illumination light emitted by the light source unit 3 during imaging is adjustable. In the following, a configuration of an endoscope device according to the fifth embodiment will be described. The same components as those of the endoscope device 1 according to, the first embodiment described above are denoted by the same reference signs, and explanation thereof will be omitted.

Configuration of Endoscope Device

Figure 28:
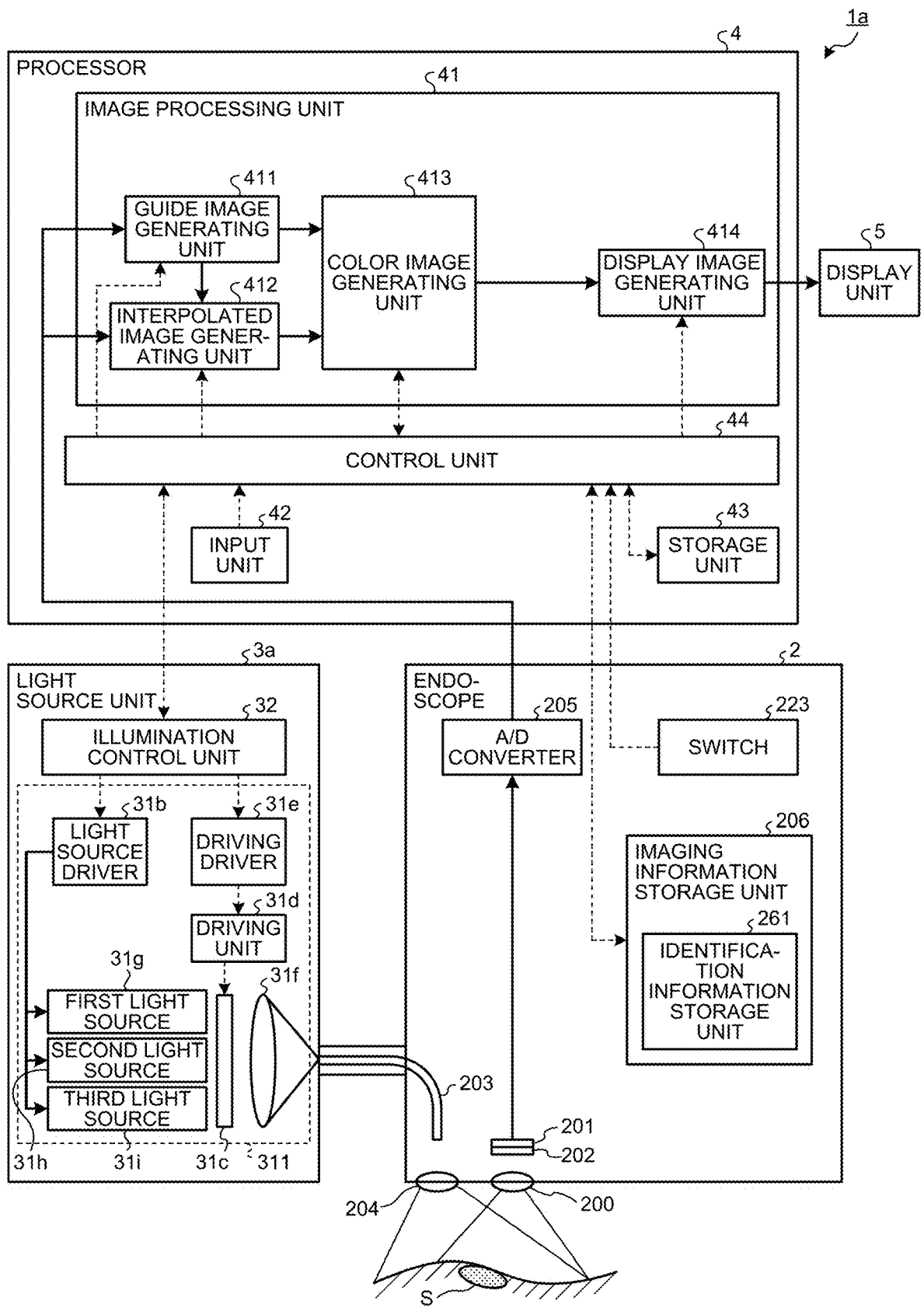
FIG. 28 is a schematic diagram illustrating an overall configuration of an endoscope device according to a fifth embodiment of the present disclosure.

FIG. 28 is a schematic diagram illustrating an overall configuration of the endoscope device according to the fifth embodiment of the present disclosure. An endoscope device 1a illustrated in FIG. 28 includes a light source unit 3a instead of the light source unit 3 of the endoscope device 1 of the first embodiment described above.

Configuration of Light Source Unit

The light source unit 3a includes an illumination unit 311 instead of the illumination unit 31 of the light source unit 3 of the first embodiment described above. The illumination unit 311 includes a first light source 31g, a second light source 31h, and a third light source 31i instead of the light source 31a of the first embodiment described above.

The first light source 31g emits light of the red wavelength band (the wavelength band of 600 nm to 700 nm) on the basis of a driving voltage input from the light source driver 31b via the illumination control unit 32 under the control of the control unit 44. The first light source 31g is configured using a light emitting diode (LED).

The second light source 31h emits light of the green wavelength band (the wavelength band of 600 nm to 500 nm) on the basis of a driving voltage input from the light source driver 31b via the illumination control unit 32 under the control of the control unit 44. The second light source 31h is configured using an LED.

The third light source 31i emits light of the blue wavelength band (the wavelength band of 390 nm to 500 nm) on the basis of a driving voltage input from the light source driver 31b via the illumination control unit 32 under the control of the control unit 44. The third light source 31i is configured using an LED.

The light source unit 3a configured as described above can emit white light by causing the first light source 31g, the second light source 31h, and the third light source 31i to concurrently emit light.

Further, according to the endoscope device 1a configured as described above, the control unit 44 changes intensity of light of the green wavelength band and intensity of light of one of the other wavelength bands, which are emitted by the illumination unit 311, via the illumination control unit 32 on the basis of the imaging signal generated by the imaging device 201 of the endoscope 2. Specifically, the control unit 44 calculates a statistical value of each of the color components in the color image generated by the image processing unit 41, and controls a spectral characteristic of illumination light emitted by the illumination unit 311 via the illumination control unit 32, in accordance with a ratio that is calculated from the statistical values. Here, the statistical value of each of the color components is an average value, a median value, or the like of the pixel values of each of the colors of the color image. More specifically, the control unit 44 calculates the statistical value of each of the color components in the color image generated by the image processing unit 41, and adjusts intensity of light emitted by each of the first light source unit 31g, the second light source unit 31h, and the third light source 31i in accordance with a ratio calculated from the statistical values. With this operation, it is possible to adjust the spectral characteristic of the illumination light depending on a subject. Further, information acquired by the Cy pixel is influenced by a spectral reflectance of the subject, and, in the case of observing an in-vivo image, it may be possible to use an observation technique of applying a pigment, such as indigo carmine, to improve the visibility of the subject. As described above, by adjusting the spectral characteristic of the illumination light emitted by the illumination unit 311 depending on the subject, the control unit 44 can obtain the same effect even in a case where a pigment is applied to observe the inside of the body.

According to the fifth embodiment of the present disclosure as described above, the control unit 44 can change intensity of light of the green wavelength band and intensity of light of one of the other wavelength bands, which are emitted by the illumination unit 311, via the illumination control unit 32 on the basis of the imaging signal generated by the imaging device 201 of the endoscope 2, and adjust the spectral characteristic of the illumination light emitted by the light source 31a depending on the subject even during imaging. Therefore, it is possible to obtain an image with high accuracy in both observation methods of the white light imaging and the narrow band imaging.

In the fifth embodiment of the present disclosure, it may be possible to allow an observer or an operator who works at the time of shipping to manually adjust the spectral characteristic of the illumination light on the basis of the statistical value of each of the color components in the color image generated by the image processing unit 41 or the color image displayed by the display unit 5. In this case, it is sufficient that the observer or the operator inputs an instruction signal for designating intensity of light emitted by each of the first light source unit 31g, the second light source unit 31h, and the third light source 31i via the input unit 42, and causes the control unit 44 to control the light source unit 3a based on the instruction signal.

Further, while the illumination unit 311 has three kinds of light sources in the fifth embodiment of the present disclosure, the embodiments are not limited to this example. For example, the illumination unit 311 may be configured to include four or more kinds of light sources. In this case, it becomes possible to more precisely adjust a spectral characteristic of the illumination light.

Other Embodiments

In the embodiments of the present disclosure, it may be possible to apply various combinations of the filters. FIG. 29 is a diagram illustrating a list, in which variations of color filters according to other embodiments of the present disclosure, wavelength bands of illumination light emitted by the light source unit 3, and effects are associated. In FIG. 29, when two kinds of complementary color pixels are used, and if they are a Cy pixel and a Ye pixel, it is sufficient to arrange the Ye filter instead of the Mg filter at the position where the Mg filter is arranged in FIG. 16 described above. Further, in FIG. 29, when two kinds of complementary color pixels are used, and if they are a Ye pixel and a Cy pixel, it is sufficient to arrange the Cy filter instead of the B filter at the position where the B filter is arranged in FIG. 23. Similarly, when two kinds of complementary color pixels are used, and if they are a Ye pixel and an Mg pixel, it is sufficient to arrange the Mg filter instead of the B filter at the position where the B filter is arranged in FIG. 23.

Furthermore, in the embodiments of the present disclosure, it may be possible to use a color filter 202f as illustrated in FIG. 30. The color filter 202f is configured such that filter units U7, each of which includes 25 filters arranged in two-dimensional 5×5 matrix, are arranged in accordance with arrangement of the pixels $P_{ij}$. The filter unit U7 includes four G filters, four B filters, one Mg filter, and 16 Cy filters. Further, the filter unit U7 is configured such that the number of the Cy filters is equal to or larger than the number of the G filters or the B filters that are most frequently arranged in the filter unit U7.

Moreover, in the embodiments of the present disclosure, a color filter 202g as illustrated in FIG. 31 may be used. The color filter 202g is configured such that filter units U8, each of which includes 36 filters arranged in two-dimensional 6×6 matrix, are arranged in accordance with arrangement of the pixels $P_{ij}$. The filter unit U8 includes nine G filters, five B filters, four Mg filters, and 18 Cy filters. Further, the filter unit U8 is configured such that the number of the Cy filters is equal to or larger than the number of the G filters that are most frequently arranged in the filter unit U8.

Furthermore, in the embodiments of the present disclosure, a color filter 202h as illustrated in FIG. 32 may be used. The color filter 202h is configured such that filter units U9, each of which includes 16 filters arranged in two-dimensional 4×4 matrix, are arranged in accordance with arrangement of the pixels $P_{ij}$. The filter unit U9 includes four G filters, two B filters, two Mg filters, and eight Cy filters. Further, the filter unit U9 is configured such that the number of the Cy filters is equal to or larger than the number of the G filters that are most frequently arranged in the filter unit U9.

Moreover, in the embodiments of the present disclosure, a color filter 202i as illustrated in FIG. 33 may be used. The color filter 202i is configured such that filter units U10, each of which includes 16 filters arranged in two-dimensional 4×4 matrix, are arranged in accordance with arrangement of the pixels $P_{ij}$. The filter unit U10 includes four G filters, two B filters, two R filters, and eight Cy filters. Further, the filter unit U10 is configured such that the number of the Cy filters is equal to or larger than the number of the G filters that are most frequently arranged in the filter unit U10.

Figure 34:
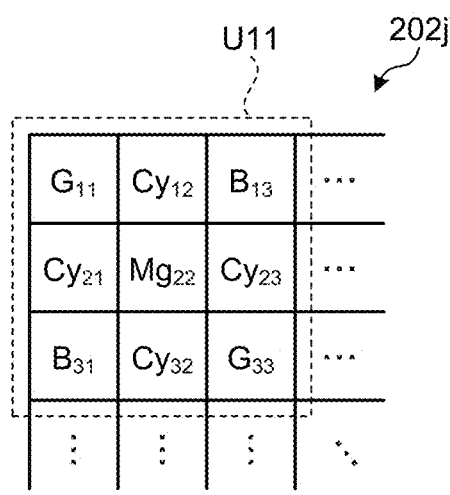
FIG. 34 is a configuration of a color filter according to still another embodiment of the present disclosure.

Furthermore, in the embodiments of the present disclosure, a color filter 202j as illustrated in FIG. 34 may be used. The color filter 202j is configured such that filter units U11, each of which includes nine filters arranged in two-dimensional 3×3 matrix, are arranged in accordance with arrangement of the pixels $P_{ij}$. The filter unit U11 includes two G filters, two B filters, one Mg filter, and four Cy filters. Further, the filter unit U11 is configured such that the number of the Cy filters is equal to or larger than the number of the G filters and/or the B filters that are most frequently arranged in the filter unit U11.

Figure 35:
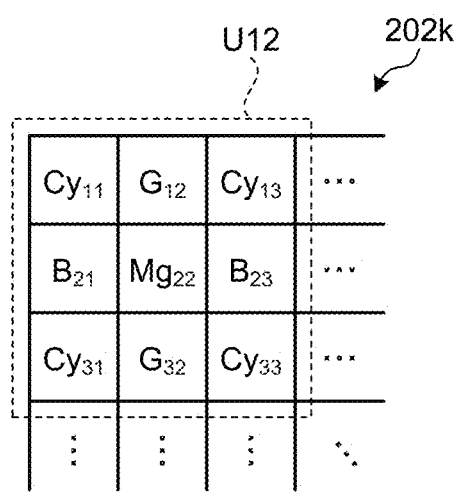
FIG. 35 is a configuration of a color filter according to still another embodiment of the present disclosure.

Moreover, in the embodiments of the present disclosure, a color filter 202k as illustrated in FIG. 35 may be used. The color filter 202k is configured such that filter units U12, each of which includes nine filters arranged in two-dimensional 3×3 matrix, are arranged in accordance with arrangement of the pixels $P_{ij}$. The filter unit U12 includes two G filters, two B filters, one Mg filter, and four Cy filters. Further, the filter unit U12 is configured such that the number of the Cy filters is equal to or larger than the number of the G filters and/or the B filters that are most frequently arranged in the filter unit U12.

Furthermore, in the embodiments of the present disclosure, a color filter 202l as illustrated in FIG. 36 may be used. The color filter 202l is configured such that filter units U13, each of which includes nine filters arranged in two-dimensional 3×3 matrix, are arranged in accordance with arrangement of the pixels $P_{ij}$. The filter unit U13 includes two G filters, one B filter, one Mg filter, and five Cy filters. Further, the filter unit U13 is configured such that the number of the Cy filters is equal to or larger than the number of the G filters that are most frequently arranged in the filter unit U13.

Moreover, in the embodiments of the present disclosure, a color filter 202m as illustrated in FIG. 37 may be used. The color filter 202m is configured such that filter units U14, each of which includes 25 filters arranged in two-dimensional 5×5 matrix, are arranged in accordance with arrangement of the pixels $P_{ij}$. The filter unit U14 includes five G filters, five B filters, three Mg filters, and 12 Cy filters. Further, the filter unit U14 is configured such that the number of the Cy filters is equal to or larger than the number of the G filters and/or the B filters that are most frequently arranged in the filter unit U14.

Figure 38:
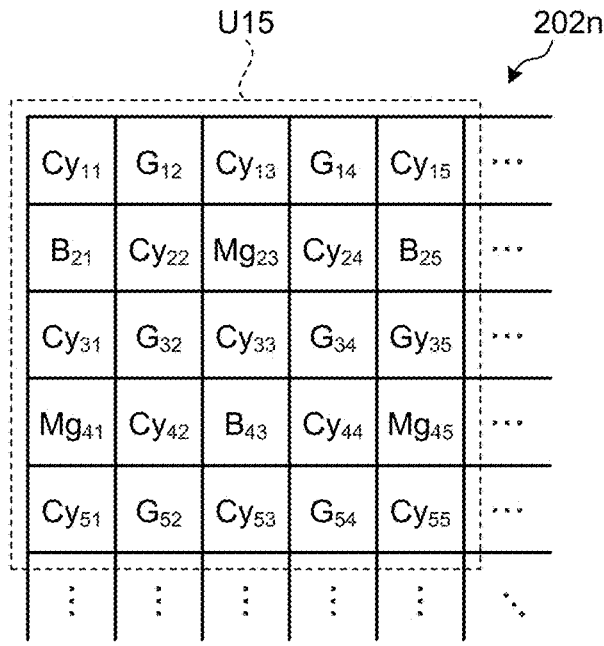
FIG. 38 is a configuration of a color filter according to still another embodiment of the present disclosure.

Furthermore, in the embodiments of the present disclosure, a color filter 202n as illustrated in FIG. 38 may be used. The color filter 202n is configured such that filter units U15, each of which includes 25 filters arranged in two-dimensional 5×5 matrix, are arranged in accordance with arrangement of the pixels $P_{ij}$. The filter unit U15 includes six G filters, three B filters, three Mg filters, and 13 Cy filters. Further, the filter unit U15 is configured such that the number of the Cy filters is equal to or larger than the number of the G filters that are most frequently arranged in the filter unit U15.

Figure 39:
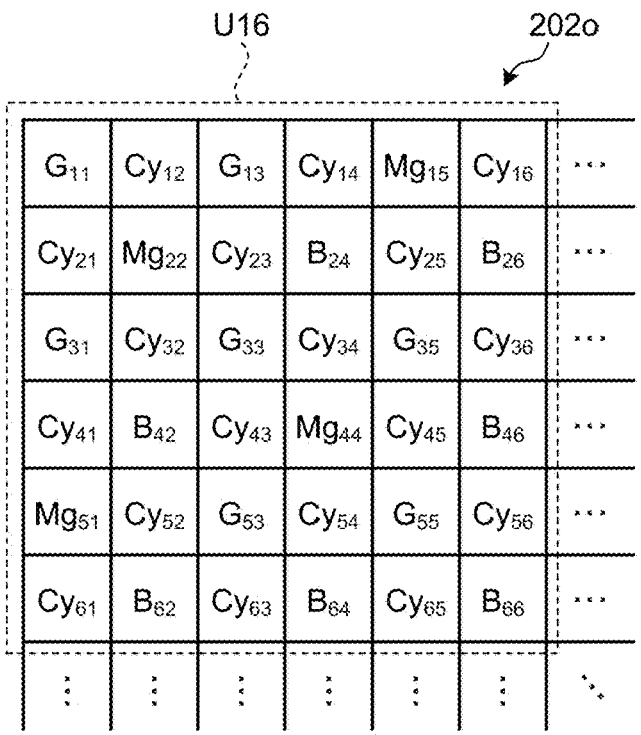
FIG. 39 is a configuration of a color filter according to still another embodiment of the present disclosure.

Moreover, in the embodiments of the present disclosure, a color filter 202o as illustrated in FIG. 39 may be used. The color filter 202o is configured such that filter units U16, each of which includes 36 filters arranged in two-dimensional 6×6 matrix, are arranged in accordance with arrangement of the pixels $P_{ij}$. The filter unit U16 includes seven G filters, seven B filters, four Mg filters, and 18 Cy filters. Further, the filter unit U16 is arranged such that the number of the Cy filters is equal to or larger than the number of the G filters and/or the B filters that are most frequently arranged in the filter unit U16.

Figure 40:
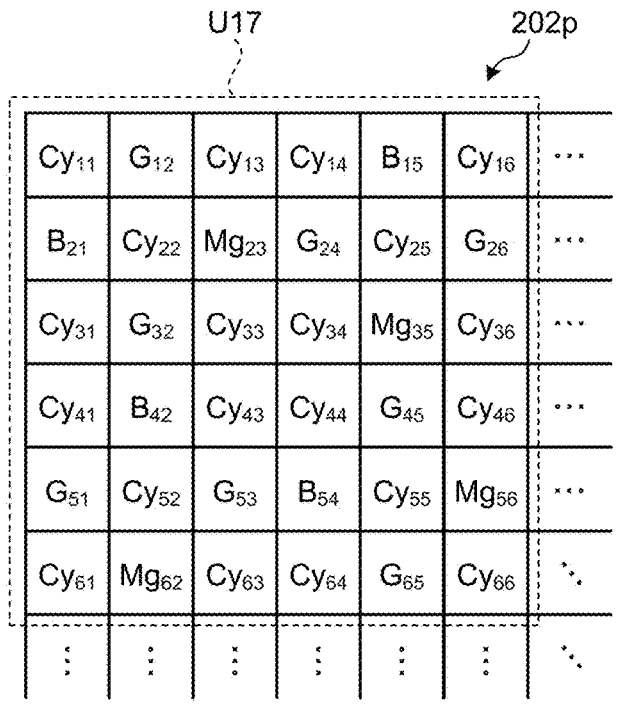
FIG. 40 is a configuration of a color filter according to still another embodiment of the present disclosure.

Furthermore, in the embodiments of the present disclosure, a color filter 202p as illustrated in FIG. 40 may be used. The color filter 202p is configured such that filter units U17, each of which includes 36 filters arranged in two-dimensional 6×6 matrix, are arranged in accordance with arrangement of the pixels P The filter unit U17 includes eight G filters, four B filters, four Mg filters, and 20 Cy filters. Further, the filter unit U17 is configured such that the number of the Cy filters is equal to or larger than the number of the G filters that are most frequently arranged in the filter unit U17.

Figure 41:
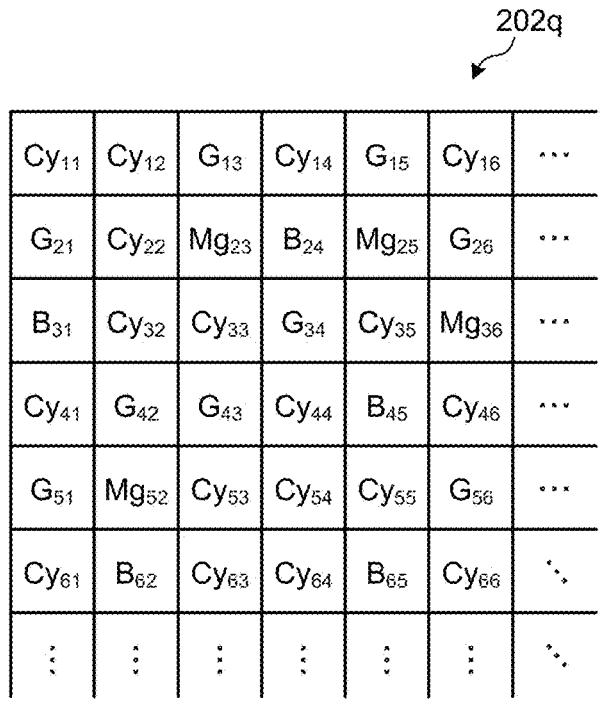
FIG. 41 is a configuration of a color filter according to still another embodiment of the present disclosure.

Moreover, in the embodiments of the present disclosure, a color filter 202q as illustrated in FIG. 41 may be used. The color filter 202q is configured such that filters arranged in a two-dimensional matrix are randomly arranged in accordance with arrangement of the pixels $P_{ij}$. The color filter 202q represents a region of 6×6 filters that are randomly arranged, and include nine G filters, five B filters, four Mg filters, and 18 Cy filters. Further, the color filter 202q is configured such that the number of the Cy filters is equal to or larger than the number of the G filters that are most frequently arranged.

The color filters 202j to 202q as described above include the Mg filter, but even when a color filter having the R filter instead of the Mg filter is used, it is possible to obtain an, image with high accuracy in both observation methods of the white light imaging and the narrow band imaging, similarly to the embodiments as described above.

Figure 42:
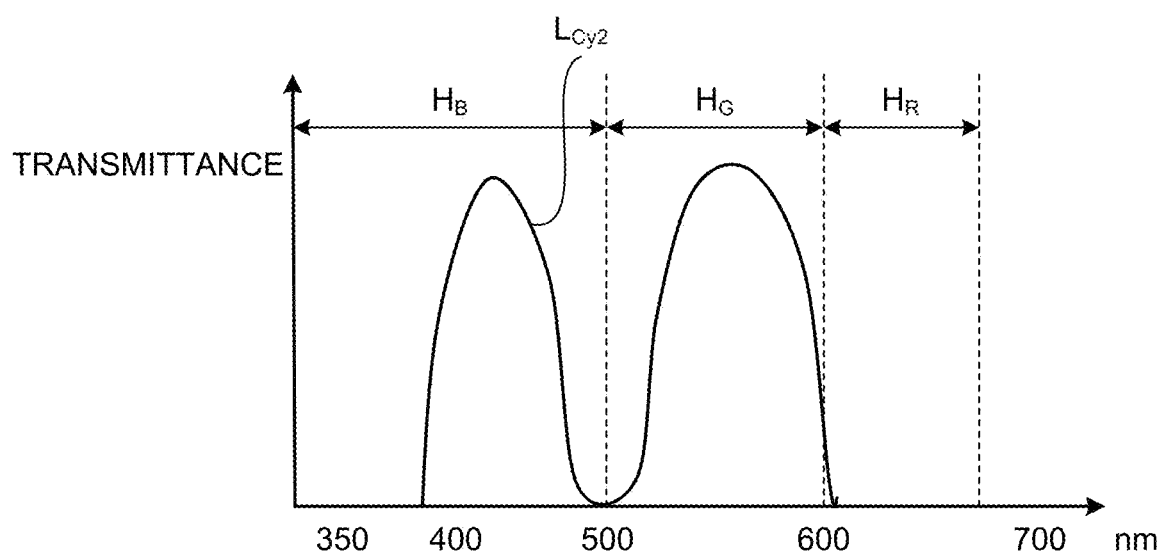
FIG. 42 is a diagram illustrating an example of a transmission characteristic of a Cy filter according to still another embodiment of the present disclosure.

Furthermore, in the embodiments of the present disclosure, the Cy filter has a transmission characteristic that enables to transmit light of the whole band of the blue wavelength band $H_B$ and the green wavelength band $H_G$; however, the Cy filter may have a bimodal transmission characteristic as indicated by a curved line $L_{Cy2}$ in FIG. 42. In this case, the image processing unit 41 can perform a color image generation process with high accuracy, so that it is possible to generate a color image with reduced noise.

Figure 43:
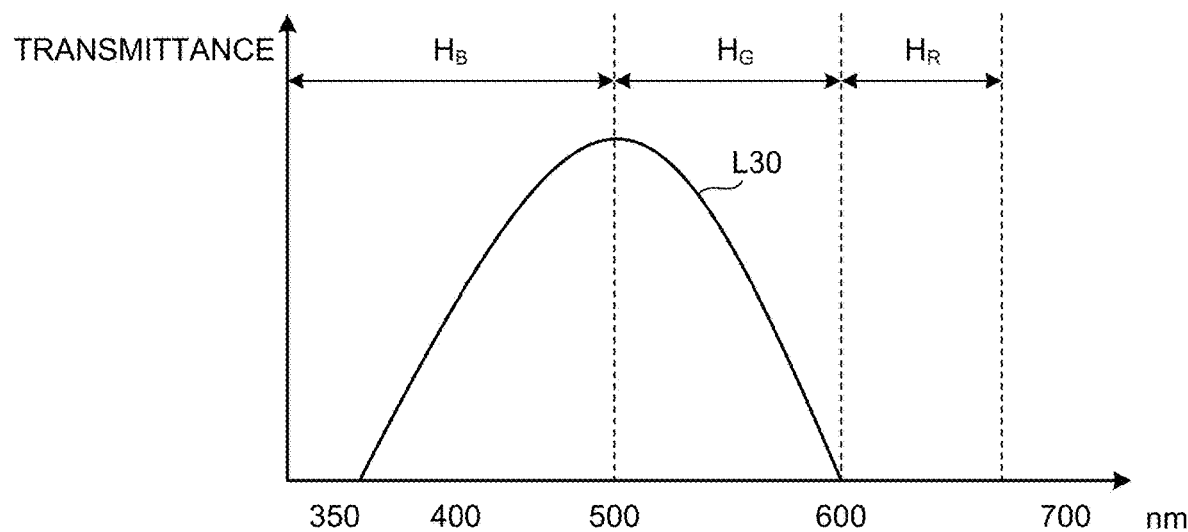
FIG. 43 is a diagram illustrating an example of a transmission characteristic of a Cy filter in a case where a light source unit according to still another embodiment of the present disclosure emits white light toward the Cy filter.
Figure 44:
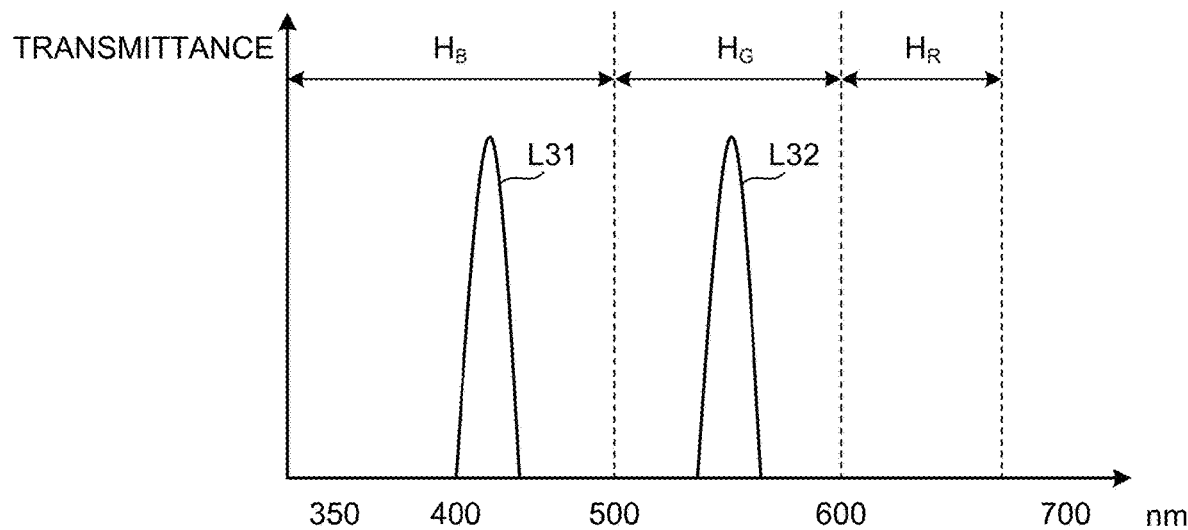
FIG. 44 is a diagram illustrating an example of a transmission characteristic of a Cy filter in a case where the light source unit according to still another embodiment of the present disclosure emits narrow band light toward the Cy filter.

Moreover, in the embodiments of the present disclosure, it may be possible to change the transmission characteristic of the Cy filter. FIG. 43 is a diagram illustrating an example of a transmission characteristic of the Cy filter in a case where the light source unit 3 emits white light toward the Cy filter. FIG. 44 is a diagram illustrating an example of a transmission characteristic of the Cy filter in a case where the light source unit 3 emits narrow band light toward the Cy filter. As indicated by a curved line L30 in FIG. 43 and curved lines L31 and L32 in FIG. 44, intensity of the blue wavelength band $H_B$ and intensity of the green wavelength band $H_G$ of the illumination light emitted from the light source unit 3 are adjusted such that integral values of amounts of transmission of light of the blue wavelength band $H_B$ and light of the green wavelength band $H_G$ on a short wavelength side and a long wavelength side with respect to a predetermined wavelength are approximately equalized. Here, the predetermined wavelength is, for example, 500 nm. Further, a condition that the integral values of the amounts of transmission are approximately equalized means that a difference between the integral value of the amounts of transmission of light of the blue wavelength band $H_B$ on the short wavelength band side with respect to the predetermined wavelength and the integral value of the amounts of transmission of light of the green wavelength band $H_G$ on the long wavelength side is 30%, or preferably 20%, or more preferably 10%. With this condition, it is possible to generate the first image with accuracy when the light source unit 3 emits the second illumination light, and generate the second image with accuracy when the light source unit 3 emits the first illumination light.

Figure 45:
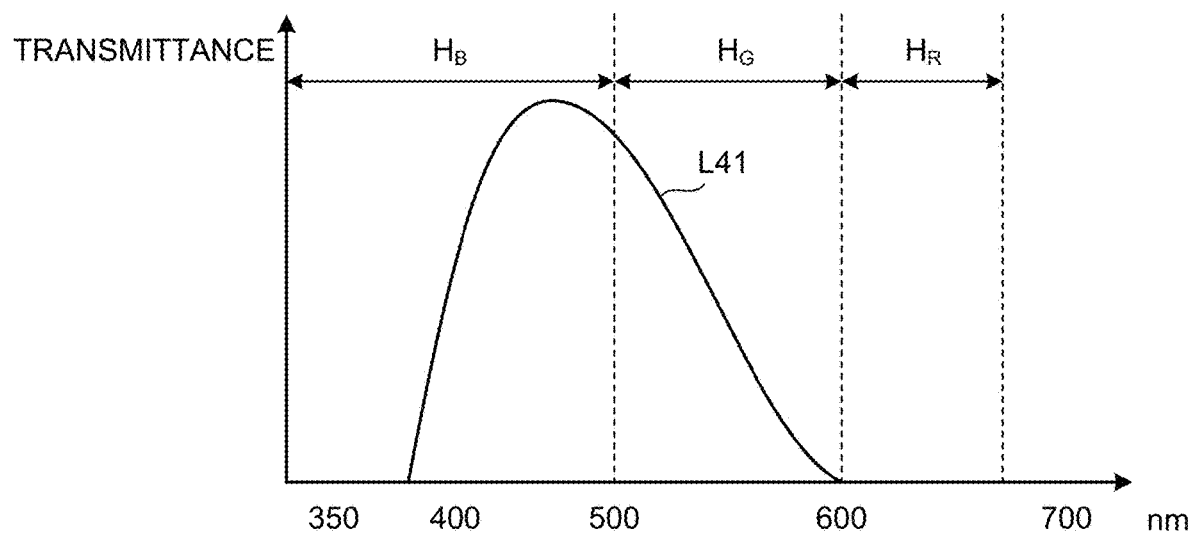
FIG. 45 is a diagram illustrating an example of a transmission characteristic of a Cy filter according to still another embodiment of the present disclosure.
Figure 46:
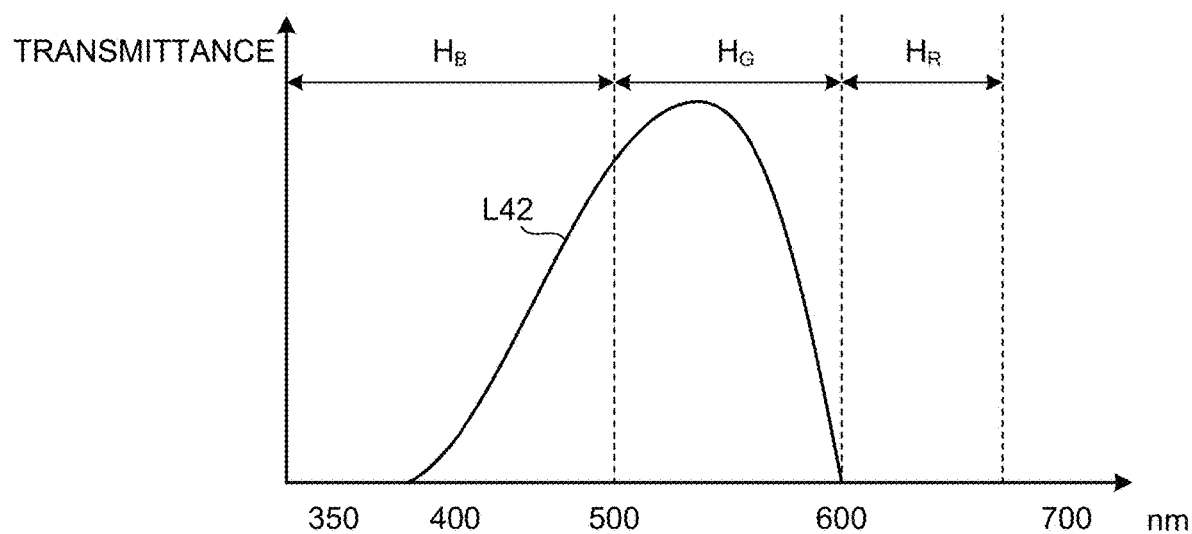
FIG. 46 is a diagram illustrating an example of a transmission characteristic of a Cy filter according to still another embodiment of the present disclosure.

Furthermore, in the present embodiments, the transmission characteristic of the Cy filter is adjusted by the spectral characteristic of the illumination light emitted by the light source unit 3, but it may be possible to use a configuration in which a transmission characteristic of a color filter is designed in accordance with the spectral characteristic of the illumination light emitted by the light source unit 3. For example, as indicated by a curved line L41 illustrated in FIG. 45 or a curved line L42 illustrated in FIG. 46, it may be possible to use a Cy filter in which a transmittance of the blue wavelength band $H_B$ and a transmittance of the green wavelength band $H_G$ are different. With this configuration, if information acquired by the Cy pixel has the characteristic as illustrated in FIG. 8 or FIG. 9 in an endoscope device, it is possible to achieve the same effect.

Moreover, in the present embodiments, illumination light emitted from the light source unit 3 is switched between the white light and the narrow band light by placing or removing the switching filter 31c into or from the optical path of the white light emitted from the single light source 31a, but it may be possible to provide a light source for emitting the white light and a light source for emitting the narrow band light, and emit the white light or the narrow band light by switching between ON and OFF of the two light sources. By providing the two light sources, the color filter, and the imaging device in a capsule casing, a capsule endoscope that is introducible into a subject may become available.

Furthermore, in the present embodiments, the image processing unit generates an interpolated image of a different color pixel by using a Cy interpolated image or a Ye interpolated image as the guide image. However, when a B interpolated image is to be generated for example, it may be possible to determine, from the Cy interpolated image, an edge direction for each of pixel positions in an image, and generate the B interpolated image only from information on B pixels on the basis of the determination result. With this configuration, it becomes possible to generate a more reliable interpolated image particularly when using a color filter in which the B filters are frequently arranged.

Moreover, while the A/D converter 205 is provided on the tip portion 24 in the endoscope device 1 according to the embodiments, the A/D converter 205 may be provided in the processor 4. Furthermore, a configuration related to the image processing may be provided in the endoscope 2, a connector that connects the endoscope 2 and the processor 4, the operating unit 22, or the like. Moreover, while the endoscope 2 connected to the processor 4 is identified using identification information or the like that is stored in the identification information storage unit 261 in the endoscope device 1 described above, it may be possible to provide an identifying element in a connection portion (connector) between the processor 4 and the endoscope 2. For example, it may be possible to provide an identification pin (identifying means) on the endoscope 2 side to identify the endoscope 2 connected to the processor 4.

While the embodiments of the present disclosure have been explained in detail above based on the drawings, the embodiments are described by way of example, and the present disclosure may be embodied in various other forms with various changes or modifications based on knowledge of a person skilled in the art, in addition to the embodiments described in this specification.

Furthermore, "a unit" recited in this specification may be replaced with "a section, a module, or a means" or "a circuitry". For example, the control unit may be replaced with a control means or a control circuitry.

According to the present disclosure, it is possible to obtain an image with high resolution in both observation methods of white light imaging and narrow band imaging.

What is claimed is:

1. An endoscope device comprising:
a light source configured to selectively emit first illumination light and second illumination light, the first illumination light including light of a red wavelength band, light of a green wavelength band, and light of a blue wavelength band, and the second illumination light including light of the green wavelength band and one of light of the blue wavelength band and light of the red wavelength band;
an imaging sensor including a plurality of pixels that are arranged in a two-dimensional matrix and configured to receive light, perform photoelectric conversion on the light, and generate imaging signals;
a color filter configured such that a plurality of filter units are arranged so as to correspond to the plurality of pixels, each of the filter units including a plurality of filters, the plurality of filters including first filters and second filters, a number of the second filters being equal to or larger than a number of a type of the first filters that is most frequently arranged in the color filter, each of the first filters being configured to transmit one of light of the red wavelength band, light of the green wavelength band, and light of the blue wavelength band, and each of the second filters being configured to transmit light of the green wavelength band and one of light of the red wavelength band and light of the blue wavelength band; and
a processor comprising hardware, the processor being configured to generate a first image corresponding to light of the green wavelength band and a second image corresponding to light of one of the other wavelength bands based on an imaging signal generated by the imaging sensor when the light source emits one of the first illumination light and the second illumination light,
wherein:
a resolution of the first image that is obtained when the light source emits the first illumination light is equal to or higher than a resolution of the first image that is obtained when the light source emits the second illumination light, and
a resolution of the second image that is obtained when the light source emits the second illumination light is higher than a resolution of the second image that is obtained when the light source emits the first illumination light.

2. The endoscope device according to claim 1, wherein:
when the light source emits the first illumination light, the second filter transmits a greater amount of light of the green wavelength band than light of one of the other wavelength bands, and
when the light source emits the second illumination light, the second filter transmits a greater amount of light of the one of the other wavelength bands than light of the green wavelength band.

3. The endoscope device according to claim 2, wherein:
when emitting the first illumination light, the light source emits light of the green wavelength band with higher intensity than light of the one of the other wavelength bands, and
when emitting the second illumination light, the light source emits light of the one of the other wavelength bands with higher intensity than light of the green wavelength band.

4. The endoscope device according to claim 1, wherein the second filter has a characteristic that, when the light source emits one of the first illumination light and the second illumination light, integral values of amounts of transmission of light of the one of the other wavelength bands and light of the green wavelength band on a short wavelength band side and a long wavelength band side with respect to a predetermined wavelength are approximately equalized.

5. The endoscope device according to claim 4, wherein when emitting one of the first illumination light and the second illumination light, the light source emits light of the green wavelength band and light of the one of the other wavelength bands such that an intensity of the light of the green wavelength band and an intensity of the light of the one of the other wavelength bands are approximately equalized.

6. The endoscope device according to claim 1, wherein the processor is further configured to change an intensity of light of the green wavelength band and an intensity of light of the one of the other wavelength bands, which are emitted by the light source, based on the imaging signal generated by the imaging sensor.

7. The endoscope device according to claim 1, wherein each of the filter units is configured such that the number of the second filters is equal to or larger than a sum of a number of the other filters arranged in each of the filter units.

8. The endoscope device according to claim 1, wherein each of the filter units is configured such that the second filters are arranged in a checkered-flag pattern.

9. The endoscope device according to claim 1, wherein the first filters are a green filter and a blue filter.

10. The endoscope device according to claim 1, wherein each of the filter units includes a third filter configured to transmit light of another one of the other wavelength bands different from the one of the other wavelength bands.

11. The endoscope device according to claim 10, wherein:
the second filter is a cyan filter, and
the third filter is a magenta filter or a yellow filter.

12. The endoscope device according to claim 10, wherein:
the second filter is a yellow filter, and
the third filter is a cyan filter or a magenta filter.

13. The endoscope device according to claim 1, wherein the processor is further configured to:
perform an interpolation process on an electrical signal that is generated by the imaging sensor based on light that has been received by a pixel via the second filter, and generate a first interpolated image for interpolating the imaging signal of a pixel on which a filter other than the second filter is arranged, and
generate, based on the first interpolated image, a second interpolated image, in which the imaging signal of the pixel on which a filter other than the second filter is arranged is interpolated, with respect to the imaging signal that is generated by the imaging sensor based on light that has been received by the pixel via the filter other than the second filter.

14. The endoscope device according to claim 1, wherein the processor is further configured to generate the first image by assuming that an electrical signal, which is generated by the imaging sensor based on light that has been received by a pixel via the second filter, corresponds to light that has been received by a pixel via the first filter.

15. An image processing apparatus connected to an endoscope provided with:
a light source configured to selectively emit first illumination light and second illumination light, the first illumination light including light of a red wavelength band, light of a green wavelength band, and light of a blue wavelength band, and the second illumination light including light of the green wavelength band and one of light of the blue wavelength band and light of the red wavelength band;
an imaging sensor including a plurality of pixels that are arranged in a two-dimensional matrix and configured to receive light, perform photoelectric conversion on the light, and generate imaging signals; and
a color filter configured such that a plurality of filter units are arranged so as to correspond to the plurality of pixels, each of the filter units including a plurality of filters, the plurality of filters including first filters and second filters, a number of the second filters being equal to or larger than a number of a type of the first filters that is most frequently arranged in the color filter, each of the first filters being configured to transmit one of light of the red wavelength band, light of the green wavelength band, and light of the blue wavelength band, and each of the second filters being configured to transmit light of the green wavelength band and one of light of the red wavelength band and light of the blue wavelength band,
the image processing apparatus comprising:
a processor comprising hardware, the processor being configured to generate a first image corresponding to light of the green wavelength band and a second image corresponding to light of one of the other wavelength bands based on an imaging signal generated by the imaging sensor when the light source emits one of the first illumination light and the second illumination light,
wherein:
a resolution of the first image that is obtained when the light source emits the first illumination light is equal to or higher than a resolution of the first image that is obtained when the light source emits the second illumination light, and
a resolution of the second image that is obtained when the light source emits the second illumination light is higher than a resolution of the second image that is obtained when the light source emits the first illumination light.

16. An image processing method performed by an image processing apparatus connected to an endoscope provided with:
a light source configured to selectively emit first illumination light and second illumination light, the first illumination light including light of a red wavelength band, light of a green wavelength band, and light of a blue wavelength band, and the second illumination light including light of the green wavelength band and one of light of the blue wavelength band and light of the red wavelength band;
an imaging sensor including a plurality of pixels that are arranged in a two-dimensional matrix and configured to receive light, perform photoelectric conversion on the light, and generate imaging signals; and
a color filter configured such that a plurality of filter units are arranged so as to correspond to the plurality of pixels, each of the filter units including a plurality of filters, the plurality of filters including first filters and second filters, a number of the second filters being equal to or larger than a number of a type of the first filters that is most frequently arranged in the color filter, each of the first filters being configured to transmit one of light of the red wavelength band, light of the green wavelength band, and light of the blue wavelength band, and each of the second filters being configured to transmit light of the green wavelength band and one of light of the red wavelength band and light of the blue wavelength band,
the image processing method comprising:
generating a first image corresponding to light of the green wavelength band and a second image corresponding to light of one of the other wavelength bands based on an imaging signal generated by the imaging sensor when the light source emits one of the first illumination light and the second illumination light, wherein:
- a resolution of the first image that is obtained when the light source emits the first illumination light is equal to or higher than a resolution of the first image that is obtained when the light source emits the second illumination light, and
- a resolution of the second image that is obtained when the light source emits the second illumination light is higher than a resolution of the second image that is obtained when the light source emits the first illumination light.

17. A non-transitory computer readable storage medium storing a program executable by an image processing apparatus connected to an endoscope provided with:
- a light source configured to selectively emit first illumination light and second illumination light, the first illumination light including light of a red wavelength band, light of a green wavelength band, and light of a blue wavelength band, and the second illumination light including light of the green wavelength band and one of light of the blue wavelength band and light of the red wavelength band;
- an imaging sensor including a plurality of pixels that are arranged in a two-dimensional matrix and configured to receive light, perform photoelectric conversion on the light, and generate imaging signals; and
- a color filter configured such that a plurality of filter units are arranged so as to correspond to the plurality of pixels, each of the filter units including a plurality of filters, the plurality of filters including first filters and second filters, a number of the second filters being equal to or larger than a number of a type of the first filters that is most frequently arranged in the color filter, each of the first filters being configured to transmit one of light of the red wavelength band, light of the green wavelength band, and light of the blue wavelength band, and each of the second filters being configured to transmit light of the green wavelength band and one of light of the red wavelength band and light of the blue wavelength band, the program being executable by the image processing apparatus to control the image processing apparatus to execute processes comprising:

generating a first image corresponding to light of the green wavelength band and a second image corresponding to light of one of the other wavelength bands based on an imaging signal generated by the imaging sensor when the light source emits one of the first illumination light and the second illumination light, wherein:
a resolution of the first image that is obtained when the light source emits the first illumination light is equal to or higher than a resolution of the first image that is obtained when the light source emits the second illumination light, and
a resolution of the second image that is obtained when the light source emits the second illumination light is higher than a resolution of the second image that is obtained when the light source emits the first illumination light.

* * * * *